(12) United States Patent
Maolinbay

(10) Patent No.: US 11,904,184 B2
(45) Date of Patent: *Feb. 20, 2024

(54) RADIATION THERAPY SYSTEMS AND METHODS WITH TUMOR TRACKING

(71) Applicant: RefleXion Medical, Inc., Hayward, CA (US)

(72) Inventor: Manat Maolinbay, Gilroy, CA (US)

(73) Assignee: RefleXion Medical, Inc., Hayward, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 18/053,874

(22) Filed: Nov. 9, 2022

(65) Prior Publication Data
US 2023/0218928 A1 Jul. 13, 2023

Related U.S. Application Data

(63) Continuation of application No. 16/582,286, filed on Sep. 25, 2019, now Pat. No. 11,504,550, which is a (Continued)

(51) Int. Cl.
A61N 5/10 (2006.01)
A61B 6/00 (2006.01)
(Continued)

(52) U.S. Cl.
CPC ............ *A61N 5/1067* (2013.01); *A61B 6/032* (2013.01); *A61B 6/06* (2013.01); *A61B 6/4085* (2013.01);
(Continued)

(58) Field of Classification Search
CPC .. A61N 5/1067; A61N 5/1047; A61N 5/1081; A61N 2005/1087;
(Continued)

(56) References Cited

U.S. PATENT DOCUMENTS 3,418,475 A 12/1968 Hudgens
3,668,399 A 6/1972 Cahill et al.
(Continued)

FOREIGN PATENT DOCUMENTS

CN 1681436 A 10/2005
CN 1799509 A 7/2006
(Continued)

OTHER PUBLICATIONS

Chang, J.Y. et al. (2008). "Image-guided radiation therapy for non-small cell lung cancer," *J. Thorac. Oncol.* 3(2):177-186.
(Continued)

*Primary Examiner* — Courtney D Thomas
(74) *Attorney, Agent, or Firm* — Cooley LLP

(57) ABSTRACT

A radiation therapy system comprising a therapeutic radiation system (e.g., an MV X-ray source, and/or a linac) and a co-planar imaging system (e.g., a kV X-ray system) on a fast rotating ring gantry frame. The therapeutic radiation system and the imaging system are separated by a gantry angle, and the gantry frame may rotate in a direction such that the imaging system leads the MV system. The radiation sources of both the therapeutic and imaging radiation systems are each collimated by a dynamic multi-leaf collimator (DMLC) disposed in the beam path of the MV X-ray source and the kV X-ray source, respectively. In one variation, the imaging system identifies patient tumor(s) positions in real-time. The DMLC for the imaging radiation source limits the kV X-ray beam spread to the tumor(s) and/or immediate tumor regions, and helps to reduce irradiation of healthy tissue (e.g., reduce the dose-area product).

20 Claims, 13 Drawing Sheets

Related U.S. Application Data continuation of application No. PCT/US2018/025252, filed on Mar. 29, 2018.

(60) Provisional application No. 62/479,045, filed on Mar. 30, 2017.

(51) Int. Cl.
*A61B 6/03* (2006.01)
*A61B 6/06* (2006.01)

(52) U.S. Cl.
CPC ......... *A61N 5/1047* (2013.01); *A61N 5/1081* (2013.01); *A61N 2005/1087* (2013.01)

(58) Field of Classification Search
CPC .... A61N 2005/1052; A61N 2005/1061; A61N 5/1049; A61B 6/032; A61B 6/06; A61B 6/4085; A61B 5/0036; A61B 5/055
See application file for complete search history.

(56) References Cited

U.S. PATENT DOCUMENTS

| | | |
|---|---|---|
| 3,767,883 A | 10/1973 | Staats |
| 3,794,840 A | 2/1974 | Scott |
| 3,869,615 A | 3/1975 | Hoover et al. |
| 3,906,233 A | 9/1975 | Vogel |
| 4,361,902 A | 11/1982 | Brandt et al. |
| 4,389,569 A | 6/1983 | Hattori et al. |
| 4,503,331 A | 3/1985 | Kovacs, Jr. et al. |
| 4,529,882 A | 7/1985 | Lee |
| 4,563,582 A | 1/1986 | Mullani |
| 4,575,868 A | 3/1986 | Ueda et al. |
| 4,628,499 A | 12/1986 | Hammett |
| 4,642,464 A | 2/1987 | Mullani |
| 4,647,779 A | 3/1987 | Wong |
| 4,677,299 A | 6/1987 | Wong |
| 4,771,785 A | 9/1988 | Duer |
| 4,868,844 A | 9/1989 | Nunan |
| 5,075,554 A | 12/1991 | Yunker et al. |
| 5,099,505 A | 3/1992 | Seppi et al. |
| 5,117,445 A | 5/1992 | Seppi et al. |
| 5,168,532 A | 12/1992 | Seppi et al. |
| 5,206,512 A | 4/1993 | Iwao |
| 5,207,223 A | 5/1993 | Adler |
| 5,272,344 A | 12/1993 | Williams |
| 5,317,616 A | 5/1994 | Swerdloff et al. |
| 5,329,567 A | 7/1994 | Ikebe |
| 5,351,280 A | 9/1994 | Swerdloff et al. |
| 5,390,225 A | 2/1995 | Hawman |
| 5,394,452 A | 2/1995 | Swerdloff et al. |
| 5,396,534 A | 3/1995 | Thomas |
| 5,418,827 A | 5/1995 | Deasy et al. |
| 5,442,675 A | 8/1995 | Swerdloff et al. |
| 5,548,627 A | 8/1996 | Swerdloff et al. |
| 5,577,026 A | 11/1996 | Gordon et al. |
| 5,661,773 A | 8/1997 | Swerdloff et al. |
| 5,668,371 A | 9/1997 | Deasy et al. |
| 5,724,400 A | 3/1998 | Swerdloff et al. |
| 5,751,781 A | 5/1998 | Brown et al. |
| 5,813,985 A | 9/1998 | Carroll |
| 5,818,902 A | 10/1998 | Yu |
| 5,851,182 A | 12/1998 | Sahadevan |
| 5,889,834 A | 3/1999 | Vilsmeier et al. |
| 5,917,883 A | 6/1999 | Khutoryansky et al. |
| 5,937,028 A | 8/1999 | Tybinkowski et al. |
| 5,946,425 A | 8/1999 | Bove, Jr. et al. |
| 6,137,114 A | 10/2000 | Rohe et al. |
| 6,180,943 B1 | 1/2001 | Lange |
| 6,184,530 B1 | 2/2001 | Hines et al. |
| 6,188,748 B1 | 2/2001 | Pastyr et al. |
| 6,255,655 B1 | 7/2001 | McCroskey et al. |
| 6,260,005 B1 | 7/2001 | Yang et al. |
| 6,271,517 B1 | 8/2001 | Kroening, Jr. et al. |
| 6,281,505 B1 | 8/2001 | Hines et al. |
| 6,385,288 B1 | 5/2002 | Kanematsu |
| 6,396,902 B2 | 5/2002 | Tybinkowski et al. |
| 6,438,202 B1 | 8/2002 | Olivera et al. |
| 6,449,331 B1 | 9/2002 | Nutt et al. |
| 6,449,340 B1 | 9/2002 | Tybinkowski et al. |
| 6,455,856 B1 | 9/2002 | Gagnon |
| 6,459,769 B1 | 10/2002 | Cosman |
| 6,504,899 B2 | 1/2003 | Pugachev et al. |
| 6,560,311 B1 | 5/2003 | Shepard et al. |
| 6,618,467 B1 | 9/2003 | Ruchala et al. |
| 6,624,451 B2 | 9/2003 | Ashley et al. |
| 6,628,744 B1 | 9/2003 | Luhta et al. |
| 6,661,866 B1 | 12/2003 | Limkeman et al. |
| 6,696,694 B2 | 2/2004 | Pastyr et al. |
| 6,700,949 B2 | 3/2004 | Susami et al. |
| 6,714,076 B1 | 3/2004 | Kalb |
| 6,730,924 B1 | 5/2004 | Pastyr et al. |
| 6,735,277 B2 | 5/2004 | McNutt et al. |
| 6,778,636 B1 | 8/2004 | Andrews |
| 6,792,078 B2 | 9/2004 | Kato et al. |
| 6,794,653 B2 | 9/2004 | Wainer et al. |
| 6,810,103 B1 | 10/2004 | Tybinkowski et al. |
| 6,810,108 B2 | 10/2004 | Clark et al. |
| 6,831,961 B1 | 12/2004 | Tybinkowski et al. |
| 6,865,254 B2 | 3/2005 | Nafstadius |
| 6,888,919 B2 | 5/2005 | Graf |
| 6,914,959 B2 | 7/2005 | Bailey et al. |
| 6,934,363 B2 | 8/2005 | Seufert |
| 6,965,661 B2 | 11/2005 | Kojima et al. |
| 6,976,784 B2 | 12/2005 | Kojima et al. |
| 6,990,175 B2 | 1/2006 | Nakashima et al. |
| 7,020,233 B1 | 3/2006 | Tybinkowski et al. |
| 7,026,622 B2 | 4/2006 | Kojima et al. |
| 7,110,808 B2 | 9/2006 | Adair |
| 7,129,495 B2 | 10/2006 | Williams et al. |
| 7,154,096 B2 | 12/2006 | Amano |
| 7,167,542 B2 | 1/2007 | Juschka et al. |
| 7,188,999 B2 | 3/2007 | Mihara et al. |
| 7,199,382 B2 | 4/2007 | Rigney et al. |
| 7,227,925 B1 | 6/2007 | Mansfield et al. |
| 7,242,750 B2 | 7/2007 | Tsujita |
| 7,263,165 B2 | 8/2007 | Ghelmansarai |
| 7,265,356 B2 | 9/2007 | Pelizzari et al. |
| 7,280,633 B2 | 10/2007 | Cheng et al. |
| 7,291,840 B2 | 11/2007 | Fritzler et al. |
| 7,297,958 B2 | 11/2007 | Kojima et al. |
| 7,298,821 B2 | 11/2007 | Ein-Gal |
| 7,301,144 B2 | 11/2007 | Williams et al. |
| 7,310,410 B2 | 12/2007 | Sohal et al. |
| 7,331,713 B2 | 2/2008 | Moyers |
| 7,338,207 B2 | 3/2008 | Gregerson et al. |
| 7,386,099 B1 | 6/2008 | Kasper et al. |
| 7,397,901 B1 | 7/2008 | Johnsen |
| 7,397,902 B2 | 7/2008 | Seeber et al. |
| 7,405,404 B1 | 7/2008 | Shah |
| 7,412,029 B2 | 8/2008 | Myles |
| 7,433,503 B2 | 10/2008 | Cherek et al. |
| 7,439,509 B1 | 10/2008 | Grazioso et al. |
| 7,446,328 B2 | 11/2008 | Rigney et al. |
| 7,453,983 B2 | 11/2008 | Schildkraut et al. |
| 7,453,984 B2 | 11/2008 | Chen et al. |
| 7,469,035 B2 | 12/2008 | Keall et al. |
| 7,496,181 B2 | 2/2009 | Mazin et al. |
| 7,545,911 B2 | 6/2009 | Rietzel et al. |
| 7,555,103 B2 | 6/2009 | Johnsen |
| 7,558,378 B2 | 7/2009 | Juschka et al. |
| 7,560,698 B2 | 7/2009 | Rietzel |
| 7,564,951 B2 | 7/2009 | Hasegawa et al. |
| 7,596,209 B2 | 9/2009 | Perkins |
| 7,627,082 B2 | 12/2009 | Kojima et al. |
| 7,639,853 B2 | 12/2009 | Olivera et al. |
| 7,656,999 B2 | 2/2010 | Hui et al. |
| 7,657,304 B2 | 2/2010 | Mansfield et al. |
| 7,679,049 B2 | 3/2010 | Rietzel |
| 7,715,606 B2 | 5/2010 | Jeung et al. |
| 7,742,575 B2 | 6/2010 | Bourne |
| 7,755,054 B1 | 7/2010 | Shah et al. |
| 7,755,055 B2 | 7/2010 | Schilling |
| 7,755,057 B2 | 7/2010 | Kim |

(56) References Cited

U.S. PATENT DOCUMENTS

| | | |
|---|---|---|
| 7,778,691 B2 | 8/2010 | Zhang et al. |
| 7,792,252 B2 | 9/2010 | Bohn |
| 7,795,590 B2 | 9/2010 | Takahashi et al. |
| 7,800,070 B2 | 9/2010 | Weinberg et al. |
| 7,820,975 B2 | 10/2010 | Laurence et al. |
| 7,826,593 B2 | 11/2010 | Svensson et al. |
| 7,839,972 B2 | 11/2010 | Ruchala et al. |
| 7,847,274 B2 | 12/2010 | Kornblau et al. |
| 7,885,371 B2 | 2/2011 | Thibault et al. |
| 7,939,808 B1 | 5/2011 | Shah et al. |
| 7,942,843 B2 | 5/2011 | Tune et al. |
| 7,952,079 B2 | 5/2011 | Neustadter et al. |
| 7,957,507 B2 | 6/2011 | Cadman |
| 7,965,819 B2 | 6/2011 | Nagata |
| 7,983,380 B2 | 7/2011 | Guertin et al. |
| 8,017,915 B2 | 9/2011 | Mazin |
| 8,019,042 B2 | 9/2011 | Shukla et al. |
| 8,059,782 B2 | 11/2011 | Brown |
| 8,063,376 B2 | 11/2011 | Maniawski et al. |
| 8,090,074 B2 | 1/2012 | Filiberti et al. |
| 8,093,568 B2 | 1/2012 | Mackie et al. |
| 8,116,427 B2 | 2/2012 | Kojima et al. |
| 8,139,713 B2 | 3/2012 | Janbakhsh |
| 8,139,714 B1 | 3/2012 | Sahadevan |
| 8,144,962 B2 | 3/2012 | Busch et al. |
| 8,148,695 B2 | 4/2012 | Takahashi et al. |
| 8,160,205 B2 | 4/2012 | Saracen et al. |
| 8,193,508 B2 | 6/2012 | Shchory et al. |
| 8,198,600 B2 | 6/2012 | Neustadter et al. |
| 8,232,535 B2 | 7/2012 | Olivera et al. |
| 8,239,002 B2 | 8/2012 | Neustadter et al. |
| 8,269,195 B2 | 9/2012 | Rigney et al. |
| 8,278,633 B2 | 10/2012 | Nord et al. |
| 8,280,002 B2 * | 10/2012 | Bani-Hashemi ...... A61N 5/1064 378/65 |
| 8,295,906 B2 | 10/2012 | Saunders et al. |
| 8,304,738 B2 | 11/2012 | Gagnon et al. |
| 8,306,185 B2 | 11/2012 | Bal et al. |
| 8,335,296 B2 | 12/2012 | Dehler et al. |
| 8,357,903 B2 | 1/2013 | Wang et al. |
| 8,384,049 B1 | 2/2013 | Broad |
| 8,395,127 B1 | 3/2013 | Frach et al. |
| 8,406,844 B2 | 3/2013 | Ruchala et al. |
| 8,406,851 B2 | 3/2013 | West et al. |
| 8,442,287 B2 | 5/2013 | Fordyce, II et al. |
| 8,461,538 B2 | 6/2013 | Mazin |
| 8,461,539 B2 | 6/2013 | Yamaya et al. |
| 8,467,497 B2 | 6/2013 | Lu et al. |
| 8,483,803 B2 | 7/2013 | Partain et al. |
| 8,509,383 B2 | 8/2013 | Lu et al. |
| 8,520,800 B2 | 8/2013 | Wilfley et al. |
| 8,536,547 B2 | 9/2013 | Maurer, Jr. et al. |
| 8,537,373 B2 | 9/2013 | Humphrey |
| 8,581,196 B2 | 11/2013 | Yamaya et al. |
| 8,588,367 B2 | 11/2013 | Busch et al. |
| 8,606,349 B2 | 12/2013 | Rousso et al. |
| 8,617,422 B2 | 12/2013 | Koschan et al. |
| 8,641,592 B2 | 2/2014 | Yu |
| 8,664,610 B2 | 3/2014 | Chuang |
| 8,664,618 B2 | 3/2014 | Yao |
| 8,712,012 B2 | 4/2014 | O'Connor |
| 8,745,789 B2 | 6/2014 | Saracen et al. |
| 8,748,825 B2 | 6/2014 | Mazin |
| 8,767,917 B2 | 7/2014 | Ruchala et al. |
| 8,816,307 B2 | 8/2014 | Kuusela et al. |
| 8,873,710 B2 | 10/2014 | Ling et al. |
| 8,884,240 B1 | 11/2014 | Shah et al. |
| 8,992,404 B2 | 3/2015 | Graf et al. |
| 9,061,141 B2 | 6/2015 | Brunker et al. |
| 9,155,909 B2 | 10/2015 | Ishikawa |
| 9,179,982 B2 | 11/2015 | Kunz et al. |
| 9,205,281 B2 | 12/2015 | Mazin |
| 9,360,570 B2 | 6/2016 | Rothfuss et al. |
| 9,370,672 B2 | 6/2016 | Parsai et al. |
| 9,437,339 B2 | 9/2016 | Echner |
| 9,437,340 B2 | 9/2016 | Echner et al. |
| 9,498,167 B2 | 11/2016 | Mostafavi et al. |
| 9,575,192 B1 | 2/2017 | Ng et al. |
| 9,649,509 B2 | 5/2017 | Mazin et al. |
| 9,697,980 B2 | 7/2017 | Ogura et al. |
| 9,731,148 B2 | 8/2017 | Olivera et al. |
| 9,820,700 B2 | 11/2017 | Mazin |
| 9,878,180 B2 | 1/2018 | Schulte et al. |
| 9,886,534 B2 | 2/2018 | Wan et al. |
| 9,952,878 B2 | 4/2018 | Grimme et al. |
| 9,974,494 B2 | 5/2018 | Mostafavi et al. |
| 10,159,853 B2 | 12/2018 | Kuusela et al. |
| 10,327,716 B2 | 6/2019 | Mazin |
| 10,478,133 B2 | 11/2019 | Levy et al. |
| 10,695,586 B2 | 6/2020 | Harper et al. |
| 10,745,253 B2 | 8/2020 | Saracen et al. |
| 10,795,037 B2 | 10/2020 | Olcott et al. |
| 11,007,384 B2 | 5/2021 | Olcott et al. |
| 11,287,540 B2 | 3/2022 | Olcott et al. |
| 11,309,072 B2 | 4/2022 | Carmi |
| 11,369,806 B2 | 6/2022 | Laurence, Jr. et al. |
| 11,504,550 B2 * | 11/2022 | Maolinbay ........... A61B 6/4085 |
| 11,511,133 B2 | 11/2022 | Olcott et al. |
| 11,675,097 B2 | 6/2023 | Olcott et al. |
| 2002/0051513 A1 | 5/2002 | Pugachev et al. |
| 2002/0148970 A1 | 10/2002 | Wong et al. |
| 2002/0163994 A1 | 11/2002 | Jones |
| 2002/0191734 A1 | 12/2002 | Kojima et al. |
| 2002/0193685 A1 | 12/2002 | Mate et al. |
| 2003/0036700 A1 | 2/2003 | Weinberg |
| 2003/0043951 A1 | 3/2003 | Akers |
| 2003/0080298 A1 | 5/2003 | Karplus et al. |
| 2003/0105397 A1 | 6/2003 | Tumer et al. |
| 2003/0128801 A1 | 7/2003 | Eisenberg et al. |
| 2003/0219098 A1 | 11/2003 | McNutt et al. |
| 2004/0024300 A1 | 2/2004 | Graf |
| 2004/0030246 A1 | 2/2004 | Townsend et al. |
| 2004/0037390 A1 | 2/2004 | Mihara et al. |
| 2004/0057575 A1 | 3/2004 | Nafstadius |
| 2004/0158416 A1 | 8/2004 | Slates |
| 2005/0028279 A1 | 2/2005 | de Mooy |
| 2005/0104001 A1 | 5/2005 | Shah |
| 2005/0109939 A1 | 5/2005 | Engler et al. |
| 2005/0213705 A1 | 9/2005 | Hoffman |
| 2005/0228255 A1 | 10/2005 | Saracen et al. |
| 2005/0234327 A1 | 10/2005 | Saracen et al. |
| 2006/0002511 A1 | 1/2006 | Miller et al. |
| 2006/0072699 A1 | 4/2006 | Mackie et al. |
| 2006/0113482 A1 | 6/2006 | Pelizzari et al. |
| 2006/0124854 A1 | 6/2006 | Shah |
| 2006/0173294 A1 | 8/2006 | Ein-Gal |
| 2006/0182326 A1 | 8/2006 | Schildkraut et al. |
| 2006/0193435 A1 | 8/2006 | Hara et al. |
| 2006/0237652 A1 | 10/2006 | Kimchy et al. |
| 2007/0003010 A1 | 1/2007 | Guertin et al. |
| 2007/0003123 A1 | 1/2007 | Fu et al. |
| 2007/0014391 A1 | 1/2007 | Mostafavi et al. |
| 2007/0023669 A1 | 2/2007 | Hefetz et al. |
| 2007/0025513 A1 | 2/2007 | Ghelmansarai |
| 2007/0043289 A1 | 2/2007 | Adair |
| 2007/0053491 A1 | 3/2007 | Schildkraut et al. |
| 2007/0055144 A1 | 3/2007 | Neustadter et al. |
| 2007/0133749 A1 | 6/2007 | Mazin et al. |
| 2007/0164239 A1 | 7/2007 | Terwilliger et al. |
| 2007/0211857 A1 | 9/2007 | Urano et al. |
| 2007/0221869 A1 | 9/2007 | Song |
| 2007/0265230 A1 | 11/2007 | Rousso et al. |
| 2007/0265528 A1 | 11/2007 | Xu et al. |
| 2007/0270693 A1 | 11/2007 | Fiedler et al. |
| 2008/0002811 A1 | 1/2008 | Allison |
| 2008/0031404 A1 | 2/2008 | Khamene et al. |
| 2008/0043910 A1 | 2/2008 | Thomas |
| 2008/0103391 A1 | 5/2008 | Dos Santos Varela |
| 2008/0128631 A1 | 6/2008 | Suhami |
| 2008/0130825 A1 | 6/2008 | Fu et al. |
| 2008/0152085 A1 | 6/2008 | Saracen et al. |
| 2008/0156993 A1 | 7/2008 | Weinberg et al. |
| 2008/0177179 A1 | 7/2008 | Stubbs et al. |
| 2008/0203309 A1 | 8/2008 | Frach et al. |

(56) References Cited

U.S. PATENT DOCUMENTS

| | | |
|---|---|---|
| 2008/0205588 A1 | 8/2008 | Kim |
| 2008/0214927 A1 | 9/2008 | Cherry et al. |
| 2008/0217541 A1 | 9/2008 | Kim |
| 2008/0230705 A1 | 9/2008 | Rousso et al. |
| 2008/0251709 A1 | 10/2008 | Cooke et al. |
| 2008/0253516 A1 | 10/2008 | Hui et al. |
| 2008/0262473 A1 | 10/2008 | Kornblau et al. |
| 2008/0273659 A1 | 11/2008 | Guertin et al. |
| 2008/0298536 A1 | 12/2008 | Ein-Gal |
| 2009/0003655 A1 | 1/2009 | Wollenweber |
| 2009/0086909 A1 | 4/2009 | Hui et al. |
| 2009/0116616 A1 | 5/2009 | Lu et al. |
| 2009/0131734 A1 | 5/2009 | Neustadter et al. |
| 2009/0169082 A1 | 7/2009 | Mizuta et al. |
| 2009/0236532 A1 | 9/2009 | Frach et al. |
| 2009/0256078 A1 | 10/2009 | Mazin |
| 2009/0309046 A1 | 12/2009 | Balakin |
| 2010/0010343 A1 | 1/2010 | Daghighian et al. |
| 2010/0040197 A1 | 2/2010 | Maniawski et al. |
| 2010/0054412 A1 | 3/2010 | Brinks et al. |
| 2010/0063384 A1 | 3/2010 | Kornblau et al. |
| 2010/0065723 A1 | 3/2010 | Burbar et al. |
| 2010/0067660 A1 | 3/2010 | Maurer, Jr. et al. |
| 2010/0069742 A1 | 3/2010 | Partain et al. |
| 2010/0074400 A1 | 3/2010 | Sendai |
| 2010/0074498 A1 | 3/2010 | Breeding et al. |
| 2010/0166274 A1 | 7/2010 | Busch et al. |
| 2010/0176309 A1 | 7/2010 | Mackie et al. |
| 2010/0198063 A1 | 8/2010 | Huber et al. |
| 2010/0237259 A1 | 9/2010 | Wang |
| 2010/0276601 A1 | 11/2010 | Duraj et al. |
| 2011/0006212 A1 | 1/2011 | Shchory et al. |
| 2011/0044429 A1 | 2/2011 | Takahashi et al. |
| 2011/0073763 A1 | 3/2011 | Subbarao |
| 2011/0092814 A1 | 4/2011 | Yamaya et al. |
| 2011/0105895 A1 | 5/2011 | Kornblau et al. |
| 2011/0105897 A1 | 5/2011 | Kornblau et al. |
| 2011/0118588 A1 | 5/2011 | Kornblau et al. |
| 2011/0198504 A1 | 8/2011 | Eigen |
| 2011/0200170 A1 | 8/2011 | Nord et al. |
| 2011/0210261 A1 | 9/2011 | Maurer, Jr. |
| 2011/0211665 A1 | 9/2011 | Maurer, Jr. et al. |
| 2011/0215248 A1 | 9/2011 | Lewellen et al. |
| 2011/0215259 A1 | 9/2011 | Iwata |
| 2011/0272600 A1 | 11/2011 | Bert et al. |
| 2011/0297833 A1 | 12/2011 | Takayama |
| 2011/0301449 A1 | 12/2011 | Maurer, Jr. |
| 2011/0309252 A1 | 12/2011 | Moriyasu et al. |
| 2011/0309255 A1 | 12/2011 | Bert et al. |
| 2011/0313231 A1 | 12/2011 | Guertin et al. |
| 2011/0313232 A1 | 12/2011 | Balakin |
| 2012/0035470 A1 | 2/2012 | Kuduvalli et al. |
| 2012/0068076 A1 | 3/2012 | Daghighian |
| 2012/0076269 A1 | 3/2012 | Roberts |
| 2012/0138806 A1 | 6/2012 | Holmes et al. |
| 2012/0161014 A1 | 6/2012 | Yamaya et al. |
| 2012/0174317 A1 | 7/2012 | Saracen et al. |
| 2012/0213334 A1 | 8/2012 | Dirauf et al. |
| 2012/0230464 A1 | 9/2012 | Ling et al. |
| 2012/0318989 A1 | 12/2012 | Park et al. |
| 2012/0323117 A1 | 12/2012 | Neustadter et al. |
| 2013/0025055 A1 | 1/2013 | Saracen et al. |
| 2013/0060134 A1 | 3/2013 | Eshima et al. |
| 2013/0092842 A1 | 4/2013 | Zhang et al. |
| 2013/0109904 A1 | 5/2013 | Siljamaki et al. |
| 2013/0111668 A1 | 5/2013 | Wiggers et al. |
| 2013/0193330 A1 | 8/2013 | Wagadarikar et al. |
| 2013/0266116 A1 | 10/2013 | Abenaim et al. |
| 2013/0279658 A1 | 10/2013 | Mazin |
| 2013/0327932 A1 | 12/2013 | Kim et al. |
| 2013/0343509 A1 | 12/2013 | Gregerson et al. |
| 2014/0029715 A1 | 1/2014 | Hansen et al. |
| 2014/0104051 A1 | 4/2014 | Breed |
| 2014/0107390 A1 | 4/2014 | Brown et al. |
| 2014/0110573 A1 | 4/2014 | Wang et al. |
| 2014/0163368 A1 | 6/2014 | Rousso et al. |
| 2014/0184197 A1 | 7/2014 | Dolinsky |
| 2014/0193336 A1 | 7/2014 | Rousso et al. |
| 2014/0217294 A1 | 8/2014 | Rothfuss et al. |
| 2014/0224963 A1 | 8/2014 | Guo et al. |
| 2014/0228613 A1 | 8/2014 | Mazin et al. |
| 2014/0239204 A1 | 8/2014 | Orton et al. |
| 2014/0257096 A1 | 9/2014 | Prevrhal et al. |
| 2014/0341351 A1 | 11/2014 | Berwick et al. |
| 2014/0355735 A1 | 12/2014 | Choi et al. |
| 2015/0018673 A1 | 1/2015 | Rose et al. |
| 2015/0035942 A1 | 2/2015 | Hampton et al. |
| 2015/0076357 A1 | 3/2015 | Frach |
| 2015/0078528 A1 | 3/2015 | Okada |
| 2015/0126801 A1 | 5/2015 | Matteo et al. |
| 2015/0131774 A1 | 5/2015 | Maurer, Jr. et al. |
| 2015/0168567 A1 | 6/2015 | Kim et al. |
| 2015/0177394 A1 | 6/2015 | Dolinsky et al. |
| 2015/0190658 A1 | 7/2015 | Yu |
| 2015/0276947 A1 | 10/2015 | Hoenk et al. |
| 2015/0285922 A1 | 10/2015 | Mintzer et al. |
| 2015/0301201 A1 | 10/2015 | Rothfuss et al. |
| 2016/0023019 A1 | 1/2016 | Filiberti et al. |
| 2016/0073977 A1 | 3/2016 | Mazin |
| 2016/0097866 A1 | 4/2016 | Williams |
| 2016/0146949 A1 | 5/2016 | Frach et al. |
| 2016/0155228 A1 | 6/2016 | Sakata et al. |
| 2016/0206203 A1 | 7/2016 | Yu et al. |
| 2016/0209515 A1 | 7/2016 | Da Silva Rodrigues et al. |
| 2016/0219686 A1 | 7/2016 | Nakayama et al. |
| 2016/0266260 A1 | 9/2016 | Preston |
| 2016/0273958 A1 | 9/2016 | Hoenk et al. |
| 2016/0287347 A1 | 10/2016 | Meier |
| 2016/0299240 A1 | 10/2016 | Cho et al. |
| 2016/0325117 A1 | 11/2016 | Arai |
| 2016/0361566 A1 | 12/2016 | Larkin et al. |
| 2016/0374632 A1 | 12/2016 | David |
| 2017/0014648 A1 | 1/2017 | Mostafavi |
| 2017/0036039 A1 | 2/2017 | Gaudio |
| 2017/0052266 A1 | 2/2017 | Kim et al. |
| 2017/0065834 A1 | 3/2017 | Lju |
| 2017/0082759 A1 | 3/2017 | Lyu et al. |
| 2017/0199284 A1 | 7/2017 | Silari et al. |
| 2017/0220709 A1 | 8/2017 | Wan et al. |
| 2017/0242136 A1 | 8/2017 | O'Neill et al. |
| 2017/0281975 A1 | 10/2017 | Filiberti et al. |
| 2018/0292550 A1 | 10/2018 | Xu et al. |
| 2019/0070437 A1 | 3/2019 | Olcott et al. |
| 2019/0126069 A1 | 5/2019 | Nord et al. |
| 2019/0282189 A1 | 9/2019 | Beneke et al. |
| 2019/0357859 A1 | 11/2019 | Mazin |
| 2020/0215355 A1 | 7/2020 | Olcott et al. |
| 2020/0368557 A1 | 11/2020 | Harper et al. |
| 2021/0196212 A1 | 7/2021 | Mazin |
| 2022/0296929 A1 | 9/2022 | Laurence, Jr. et al. |
| 2022/0395707 A1 | 12/2022 | Laurence, Jr. et al. |

FOREIGN PATENT DOCUMENTS

| | | |
|---|---|---|
| CN | 1960780 A | 5/2007 |
| CN | 101297759 A | 11/2008 |
| CN | 101378805 A | 3/2009 |
| CN | 101803929 A | 8/2010 |
| CN | 101970043 A | 2/2011 |
| CN | 103071241 A | 5/2013 |
| CN | 103648392 A | 3/2014 |
| CN | 103650095 A | 3/2014 |
| CN | 105073188 A | 11/2015 |
| CN | 106461801 A | 2/2017 |
| DE | 10-2008-053321 A1 | 5/2010 |
| DE | 10-2013-205606 A1 | 10/2014 |
| EP | 0 437 434 A1 | 7/1995 |
| EP | 0 817 978 A1 | 8/2001 |
| EP | 0 984 393 B1 | 3/2007 |
| EP | 1 762 177 A2 | 3/2007 |
| EP | 1 501 604 B1 | 12/2009 |
| EP | 1 898 234 B1 | 4/2010 |
| EP | 2 188 815 B1 | 11/2011 |
| EP | 2 687 259 A1 | 1/2014 |

(56) References Cited

FOREIGN PATENT DOCUMENTS

| | | |
|---|---|---|
| EP | 2 872 913 B1 | 2/2016 |
| EP | 2 874 702 B1 | 9/2016 |
| EP | 1 664 752 B1 | 6/2017 |
| FR | 2839894 A1 | 11/2003 |
| GB | 69634119 T2 | 2/2006 |
| GB | 2513596 A | 11/2014 |
| IL | 208396 | 12/2010 |
| JP | H-01-156830 A | 6/1989 |
| JP | H-09-122110 A | 5/1997 |
| JP | 2002-263090 A | 9/2002 |
| JP | 2003-534823 A | 11/2003 |
| JP | 2007-502166 A | 2/2007 |
| JP | 2007-507246 A | 3/2007 |
| JP | 2008-173184 A | 7/2008 |
| JP | 2008-173299 A | 7/2008 |
| JP | 2010-500910 A | 1/2010 |
| JP | 2011-007614 A | 1/2011 |
| JP | 2011-508654 A | 3/2011 |
| JP | 2011-514213 A | 5/2011 |
| JP | 2012-042344 A | 3/2012 |
| JP | 2012-129984 A | 7/2012 |
| JP | 2012-254146 A | 12/2012 |
| JP | 2013-257320 A | 12/2013 |
| JP | 2013-545560 A | 12/2013 |
| JP | 2014-521370 A | 8/2014 |
| NL | 9520013 A | 2/1997 |
| WO | WO-89/10090 A1 | 11/1989 |
| WO | WO-95/22241 A1 | 8/1995 |
| WO | WO-00/15299 A1 | 3/2000 |
| WO | WO-2004/017832 A2 | 3/2004 |
| WO | WO-2004/017832 A3 | 3/2004 |
| WO | WO-2004/105574 A2 | 12/2004 |
| WO | WO-2004/105574 A3 | 12/2004 |
| WO | WO-2005/018734 A2 | 3/2005 |
| WO | WO-2005/018734 A3 | 3/2005 |
| WO | WO-2005/018735 A2 | 3/2005 |
| WO | WO-2005/018735 A3 | 3/2005 |
| WO | WO-2005/110495 A1 | 11/2005 |
| WO | WO-2007/045076 A1 | 4/2007 |
| WO | WO-2007/094002 A2 | 8/2007 |
| WO | WO-2007/094002 A3 | 8/2007 |
| WO | WO-2007/124760 A1 | 11/2007 |
| WO | WO-2008/019118 A2 | 2/2008 |
| WO | WO-2008/019118 A3 | 2/2008 |
| WO | WO-2008/024463 A2 | 2/2008 |
| WO | WO-2008/024463 A3 | 2/2008 |
| WO | WO-2009/114117 A2 | 9/2009 |
| WO | WO-2009/114117 A3 | 9/2009 |
| WO | WO-2010/015358 A1 | 2/2010 |
| WO | WO-2010/109585 A1 | 9/2010 |
| WO | WO-2010/110255 A1 | 9/2010 |
| WO | WO-2012/135771 A1 | 10/2012 |
| WO | WO-2013/168043 A2 | 11/2013 |
| WO | WO-2013/168043 A3 | 11/2013 |
| WO | WO-2015/038832 A1 | 3/2015 |
| WO | WO-2015/042510 A1 | 3/2015 |
| WO | WO-2015/103564 A1 | 7/2015 |
| WO | WO-2015/134953 A1 | 9/2015 |
| WO | WO-2015/161036 A1 | 10/2015 |
| WO | WO-2016/097977 A1 | 6/2016 |
| WO | WO-2016/203822 A1 | 12/2016 |

OTHER PUBLICATIONS

Chen, Y. et al. (2011). Dynamic tomotherapy delivery, *Am. Assoc. Phys. Med.* 38:3013-3024.
Corrected Notice of Allowability dated Jan. 29, 2020, for U.S. Appl. No. 16/100,054, filed Aug. 9, 2018, 4 pages.
Corrected Notice of Allowability dated May 17, 2022, for U.S. Appl. No. 16/191,131, filed Nov. 14, 2018, 8 pages.
Corrected Notice of Allowability dated Feb. 14, 2023, for U.S. Appl. No. 17/697,828, filed Mar. 17, 2022, 4 pages.
Corrected Notice of Allowability dated Feb. 23, 2023, for U.S. Appl. No. 17/697,828, filed Mar. 17, 2022, 2 pages.
Corrected Notice of Allowability dated Mar. 16, 2023, for U.S. Appl. No. 17/203,532, filed Mar. 16, 2021, 2 pages.
Dieterich, S. et al. (2003). "Skin respiratory motion tracking for stereotactic radiosurgery using the CyberKnife," *Elsevier Int'l Congress Series* 1256:130-136.
Erdi, Y.E. (2007). "The use of PET for radiotherapy," *Curr. Medical Imaging Reviews* 3(1):3-16.
Extended European Search Report dated Mar. 31, 2017, for European Application No. 09 719 473.2, filed on Mar. 9, 2009, 8 pages.
Extended European Search Report dated Jun. 9, 2020, for EP Application No. 17 871 349.1, filed on Nov. 15, 2017, 6 pages.
Extended European Search Report dated Apr. 1, 2021, for EP Application No. 18 844 237.0, filed on Aug. 9, 2018, 8 pages.
Extended European Search Report dated May 26, 2021, for EP Application No. 18 832 571.6, filed on Jul. 11, 2018, 9 pages.
Extended European Search Report dated Mar. 30, 2022, for EP Application No. 21 195 331.0, filed on Nov. 15, 2017, 11 pages.
Fan, Q. et al. (2012). "Emission Guided Radiation Therapy for Lung and Prostrate Cancers: A Feasibility Study on a Digital Patient," *Med. Phys.* 39(11):7140-7152.
Fan, Q. et al. (2013). "Toward a Planning Scheme for Emission Guided Radiation Therapy (EGRT): FDG Based Tumor Tracking in a Metastatic Breast Cancer Patient," *Med. Phys.* 40(8): 12 pages.
Final Office Action dated Aug. 15, 2012, for U.S. Appl. No. 13/209,275, filed Aug. 12, 2011, 8 pages.
Final Office Action dated Jan. 11, 2022, for U.S. Appl. No. 16/191,131, filed Nov. 14, 2018, 25 pages.
Galvin, J.M. (2018). "The multileaf collimator—A complete guide," 17 total pages.
Gibbons, J.P. (2004). "Dose calculation and verification for tomotherapy," 2004 ACMP Meeting, Scottsdale, AZ., 71 total pages.
Glendinning, A.G. et al. (2001). "Measurement of the response of $Gd_2O_2S$:Tb phosphor to 6 MV x-rays," *Phys. Mol. Biol.* 46:517-530.
Handsfield, L.L. et al. (2014). "Phantomless patient-specific TomoTherapy QA via delivery performance monitoring and a secondary Monte Carlo dose calculation," *Med. Phys.* 41:101703-1-101703-9.
International Search Report dated May 4, 2009, for PCT Application No. PCT/US2009/01500, filed on Mar. 9, 2009, 3 pages.
International Search Report dated Mar. 7, 2018, for PCT Application No. PCT/US2017/061848, filed on Nov. 15, 2017, 4 pages.
International Search Report dated Oct. 2, 2018, for PCT Application No. PCT/US2018/041700, filed on Jul. 11, 2018, 2 pages.
International Search Report dated Oct. 24, 2018, for PCT Application No. PCT/US2018/046132, filed on Aug. 9, 2018, 2 pages.
International Search Report dated Mar. 13, 2018, for PCT Application No. PCT/US2017/061855, filed on Nov. 15, 2017, 4 pages.
International Search Report dated Jun. 20, 2018, for PCT Application No. PCT/US2018/025252, filed on Mar. 29, 2018, 2 pages.
International Search Report dated Jan. 30, 2019, for PCT Application No. PCT/US2018/061099, filed on Nov. 14, 2018, 4 pages.
Kapatoes, J.M. et al. (2001). "A feasible method for clinical delivery verification and dose reconstruction in tomotherapy," *Med. Phys.* 28:528-542.
Keall, P.J. et al. (2001). "Motion adaptive x-ray therapy: a feasibility study," *Phys. Med. Biol.* 46:1-10.
Kim, H. et al. (2009). "A multi-threshold method for the TOF-PET Signal Processing," *Nucl. Instrum. Meth. Phys. Res. A*. 602:618-621.
Krouglicof, N. et al. (2013). "Development of a Novel PCB-Based Voice Coil Actuator for Opto-Mechatronic Applications," *presented at IEEE/RSJ International Conference on Intelligent Robots and Systems (IROS)*, Tokyo, Japan, Nov. 3-7, 2013, pp. 5834-5840.
Langen, K.M. et al. (2010). "QA for helical tomotherapy: report of the AAPM Task Group 148," *Med. Phys.* 37:4817-4853.
Li, X. et al. (2016). "Timing calibration for Time-of-Flight PET using positron-emitting isotopes and annihilation targets," *IEEE Transactions on Nuclear Science* 63:1351-1358.
Lu, W. (2009). "Real-time motion-adaptive-optimization (MAO) in tomotherapy," *Phys. Med. Biol.* 54:4373-4398.

(56) References Cited

OTHER PUBLICATIONS

Lu, W. (2008). "Real-time motion-adaptive delivery (MAD) using binary MLC: I. Static beam (topotherapy) delivery," Phys. Med. Biol. 53:6491-6511.
Mackie, T.R. et al. (Nov.-Dec. 1993). "Tomotherapy: A New Concept for the Delivery of Dynamic Conformal Radiotherapy," Med. Phys. 20(6):1709-1719.
McMahon, R. et al. (2008). "A real-time dynamic-MLC control algorithm for delivering IMRT to targets undergoing 2D rigid motion in the beam's eye view," Med. Phys. 35:3875-3888.
Mazin, S. R. et al. (2010). "Emission-Guided Radiation Therapy: Biologic Targeting and Adaptive Treatment," *Journal of American College of Radiology* 7(12):989-990.
Non-Final Office Action dated Jan. 10, 2011, for U.S. Appl. No. 12/367,679, filed Feb. 9, 2009, 9 pages.
Non-Final Office Action dated Feb. 28, 2012, for U.S. Appl. No. 13/209,275, filed Aug. 12, 2011, 8 pages.
Non-Final Office Action dated Sep. 19, 2013, for U.S. Appl. No. 13/895,255, filed May 15, 2013, 8 pages.
Non-Final Office Action dated Jan. 7, 2020, for U.S. Appl. No. 15/814,222, filed Nov. 15, 2017, 13 pages.
Non-Final Office Action dated Oct. 5, 2020, for U.S. Appl. No. 16/887,896, filed May 29, 2020, 62 pages.
Non-Final Office Action dated Nov. 3, 2020, for U.S. Appl. No. 16/818,325, filed Mar. 13, 2020, 9 pages.
Non-Final Office Action dated Mar. 12, 2021, for U.S. Appl. No. 16/887,896, filed May 29, 2020, 64 pages.
Non-Final Office Action dated Apr. 26, 2021, for U.S. Appl. No. 16/191,131, filed Nov. 14, 2018, 28 pages.
Non-Final Office Action dated Dec. 14, 2022, for U.S. Appl. No. 16/887,852, filed May 29, 2020, 12 pages.
Non-Final Office Action dated Jan. 17, 2023, for U.S. Appl. No. 17/837,900, filed Jun. 10, 2022, 12 pages.
Non-Final Office Action dated Jan. 20, 2023, for U.S. Appl. No. 17/852,067, filed Jun. 28, 2022, 21 pages.
Notice of Allowance dated Jul. 25, 2011, for U.S. Appl. No. 12/367,679, filed Feb. 9, 2009, 7 pages.
Notice of Allowance dated Apr. 9, 2014, for U.S. Appl. No. 13/895,255, filed May 15, 2013, 7 pages.
Notice of Allowance dated Oct. 27, 2015, for U.S. Appl. No. 14/278,973, filed May 15, 2014, 8 pages.
Notice of Allowance dated Mar. 27, 2013, for U.S. Appl. No. 13/209,275, filed Aug. 12, 2011, 9 pages.
Notice of Allowance dated Oct. 5, 2017, for U.S. Appl. No. 14/951,194, filed Nov. 24, 2015, 11 pages.
Notice of Allowance dated Apr. 4, 2019, for U.S. Appl. No. 15/807,383, filed Nov. 8, 2017, 11 pages.
Notice of Allowance dated Dec. 4, 2019, for U.S. Appl. No. 16/100,054, filed Aug. 9, 2018, 13 pages.
Notice of Allowance dated Apr. 10, 2020, for U.S. Appl. No. 16/033,125, filed Jul. 11, 2018, 18 pages.
Notice of Allowance dated Apr. 30, 2020, for U.S. Appl. No. 15/814,222, filed Nov. 15, 2017, 10 pages.
Notice of Allowance dated Feb. 22, 2021, for U.S. Appl. No. 16/818,325, filed Mar. 13, 2020, 7 pages.
Notice of Allowance dated Dec. 22, 2021, for U.S. Appl. No. 16/887,896, filed May 29, 2020, 11 pages.
Notice of Allowance dated Apr. 29, 2022, for U.S. Appl. No. 16/191,131, filed Nov. 14, 2018, 11 pages.
Notice of Allowance dated Jun. 30, 2022, for U.S. Appl. No. 16/582,286, filed Sep. 25, 2019, 10 pages.
Notice of Allowance dated Jul. 12, 2022, for U.S. Appl. No. 17/238,113, filed Apr. 22, 2021, 9 pages.
Notice of Allowance dated Jul. 21, 2022, for U.S. Appl. No. 16/582,286, filed Sep. 25, 2019, 7 pages.
Notice of Allowance dated Aug. 1, 2022, for U.S. Appl. No. 17/238,113, filed Apr. 22, 2021, 8 pages.
Notice of Allowance dated Dec. 15, 2022, for U.S. Appl. No. 17/203,532, filed Mar. 16, 2021, 8 pages.
Notice of Allowance dated Feb. 7, 2023, for U.S. Appl. No. 17/697,828, filed Mar. 17, 2022, 10 pages.
North Shore LIJ (2008). IMRT treatment plans: Dosimetry measurements & monitor units validation, 133 total pages.
Olivera, G.H. et al. (2000). "Modifying a plan delivery without re-optimization to account for patient offset in tomotherapy," Proceedings of the $22^{nd}$ Annual EMBS International Conference, Jul. 23-28, 2000, Chicago, IL, pp. 441-444.
Papanikolaou, N. et al. (2010). "MU-Tomo: Independent dose validation software for helical tomo therapy," *J. Cancer Sci. Ther.* 2:145-152.
Parodi, K. (2015). "Vision 20/20: Positron emission tomography in radiation therapy planning, delivery, and monitoring," *Med. Phys.* 42:7153-7168.
Prabhakar, R. et al. (2007). "An Insight into PET-CT Based Radiotherapy Treatment Planning," *Cancer Therapy* (5):519-524.
Schleifring (2013). Slip Ring Solutions—Technology, 8 total pages.
Tashima, H. et al. (2012). "A Single-Ring Open PET Enabling PET Imaging During Radiotherapy," *Phys. Med. Biol.* 57(14):4705-4718.
TomoTherapy® (2011). TOMOHD Treatment System, Product Specifications, 12 total pages.
Varian Medical Systems (2004). "Dynamic Targeting™ Image-Guided Radiation Therapy—A Revolution in Cancer Care," *Business Briefing: US Oncology Review*, Abstract only, 2 pages.
ViewRay's MRIDIAN LINAC enables radiosurgery with MRI vision for cancer therapy, (2017). YouTube video located at https://www.youtube.com/watch?v=zm3g-BISYDQ, PDF of Video Screenshot Provided.
Wang, D. et al. (2006). "Initial experience of FDG-PET/CT guided IMRT of head-and-neck carcinoma," Int. J. Radiation Oncology Biol. Phys. 65:143-151.
Wikipedia (2016). "Scotch yoke," Retrieved from https://en.wikipedia.org/wiki/Scotch_yoke, 3 pages.
Willoughby, T. et al. (2012). "Quality assurance for nonradiographic radiotherapy localization and positioning systems: Report of task group 147," Med. Phys. 39:1728-1747.
Written Opinion of the International Searching Authority dated May 4, 2009, for PCT Application No. PCT/US2009/01500, filed on Mar. 9, 2009, 5 pages.
Written Opinion of the International Searching Authority dated Mar. 7, 2018, for PCT Application No. PCT/US2017/061848, filed on Nov. 15, 2017, 5 pages.
Written Opinion of the International Searching Authority dated Oct. 2, 2018, for PCT Application No. PCT/US2018/041700, filed on Jul. 11, 2018, 19 pages.
Written Opinion of the International Searching Authority dated Oct. 24, 2018, for PCT Application No. PCT/US2018/046132, filed on Aug. 9, 2018, 7 pages.
Written Opinion of the International Searching Authority dated Mar. 13, 2018, for PCT Application No. PCT/US2017/061855, filed on Nov. 15, 2017, 6 pages.
Written Opinion of the International Searching Authority dated Jun. 20, 2018, for PCT Application No. PCT/US2018/025252, filed on Mar. 29, 2018, 12 pages.
Written Opinion of the International Searching Authority dated Jan. 30, 2019, for PCT Application No. PCT/US2018/061099, filed on Nov. 14, 2018, 11 pages.
Yamaya, T. et al. (2008). "A proposal of an open PET geometry," *Physics in Med. and Biology* 53:757-773.
Final Office Action dated Aug. 10, 2021, for U.S. Appl. No. 16/887,896, filed May 29, 2020, 66 pages.
Final Office Action dated Aug. 22, 2023, for U.S. Appl. No. 17/852,067, filed Jun. 28, 2022, 23 pages.
Final Office Action dated Sep. 19, 2023, for U.S. Appl. No. 17/837,900, filed Jun. 10, 2022, 16 pages.

\* cited by examiner

| System Parameters | Nominal Values | Comments |
|---|---|---|
| Lung tumor speed (cm/s) | 1 | Typical lung inhale/exhale on S-I direction |
| kV to MV tumor tracking lag distance (cm) | 0.1 | This is due to the tumor motion between kV imaging and MV firing |
| Tracking lag in time (s) | 0.1 | This is the time lag from kV imaging to MV firing |
| Treatment FOV in X-direction at ISO (cm) | 40 | Can treat multiple tumors bound in the FOV concurrently. |
| Treatment FOV in Z-direction at ISO (cm) | 15 | Along this MLC leaf direction, only non-overlapping tumors can be treated. |
| Gantry rotation Time (s) | 0.80 | The shorter rotation time, the smaller the tracking lag. |
| MV and kV ring diameter | 200 | Larger ring diameter is favored for smaller MV-kV angle. |
| MV or kV source to ISO distance (cm) | 100 | The MV and kV systems has the same geometry. |
| Bore diameter | 80 | |
| ISO center to MV or kV detectors (cm) | 100 | Larger air gap is important for reducing the scatter from the patient and better image quality |
| Detector size (MV and kV) X-direction (cm) | 80 | Both can be flat panel detectors, typical 60 frame per second |
| Detector size (MV and kV) Z-direction (cm) | 30 | |
| Detector pixel pitch (mm) | 1 | The corresponding resolution at the ISO is 0.5mm. |
| Gap between MV-kV detectors | 1.43 | |
| Central angle between MV and KV | 45 | The angle is physically limited by FOV-X size. |
| Number of firing positions | 48 | The MV and kV systems can be programmed to firing at these fixed positions. They can also fire at any positions. |
| Angle between adjacent firing positions (degree) | 7.5 | |
| MV to KV distance at the source (cm) | 82.9 | Space for the MV Linac and kV X-ray tube |
| Dynamic MLC leaf transition time (ms) | 16.7 | Adequate leaf speed |

FIG. 1B

Tum_$a_n$

RADIATION THERAPY SYSTEMS AND METHODS WITH TUMOR TRACKING

CROSS-REFERENCE TO RELATED APPLICATIONS

This application is a continuation of U.S. application Ser. No. 16/582,286, filed Sep. 25, 2019, and a continuation of International Patent Application No. PCT/US2018/025252, filed Mar. 29, 2018, which claims priority to U.S. Provisional Patent Application No. 62/479,045, filed Mar. 30, 2017, the disclosures of each of which are hereby incorporated by reference in their entireties.

TECHNICAL FIELD

This disclosure relates to a radiation therapy system comprising an imaging system and a therapeutic radiation system. The imaging system may provide real-time images and/or image data of patient regions of interest (ROI). These images and/or data may be used by the therapeutic radiation system to direct radiation to ROIs, while limiting the irradiation of other patient regions (e.g., organs at risk (OARs) and/or healthy tissue). In one variation, the imaging system and the therapeutic radiation system are both mounted on a high-speed rotatable gantry (e.g., about 30 RPM to about 70 RPM). The imaging system comprises a kV X-ray source and a multi-leaf collimator disposed in the kV X-ray beam path and the therapeutic radiation system comprises an MV X-ray source and another multi-leaf collimator disposed in the MV X-ray beam path.

BACKGROUND

In modern intensity modulated radiation therapy (IMRT), real-time tracking of moving tumor targets during a treatment session is a challenging problem. Uncertainty or imprecise knowledge of a tumor location may result in irradiation of healthy tissue and under-dosing tumor tissue. Many techniques have been developed to manage the problems that may arise from tumor motion. Some techniques include respiratory gating and/or imaging the patient prior to treatment (such as image guided radiation therapy (IGRT). A variety of imaging modalities may be used to guide a radiation therapy session, for example, X-ray or CT, PET and MRI. While these technologies may provide improved accuracy of dose delivery to the tumors while reducing the irradiation of surrounding healthy tissues, they may introduce other complications. For example, some IGRT techniques may involve implanting fiducial markers, increased levels of radiation exposure to the patient, and/or increased systems costs.

For example, tumor-tracking using kV X-ray fluoroscopy may provide some real-time information on tumor location during a treatment session, however, the location data may be inaccurate due to poor image quality and/or anatomical clutter (e.g., bones, blood vessels and other tissues). Improving imaging quality for radiation-based imaging modalities often involves exposing the patient to increasing levels of radiation (e.g., levels greater than 1.5-2.5 µR/frame). Because the image contrast to noise ratio (CNR) improves with the square root of X-ray exposure, the amount of X-rays must be significantly increased in order to attain an appreciable improvement in image quality. However, increasing X-ray emissions also increases the amount of scattered X-rays, and may also enlarge the exposure area. Anatomical structures that overlap with tumor(s) (e.g., in projection X-ray images) may make it difficult to precisely detect and locate the tumor(s).

Accordingly, systems and methods that provide improved precision in tumor location while reducing overall patient radiation exposure may be desirable.

SUMMARY

Disclosed herein are systems and methods for real-time tumor imaging during a radiation therapy session. The systems and methods described herein may enable the acquisition of tumor images that have higher levels of image contrast and quality (e.g., to improve the contrast-to-noise ratio or CNR by as much as a factor of ten) to provide tumor location data for radiation therapy (e.g., intensity modulated radiation therapy or IMRT, image guided radiation therapy or IGRT, emission guided radiation therapy or EGRT). One variation of a radiation therapy system may comprise a rotatable gantry, an imaging system mounted on the gantry, and a therapeutic radiation system also mounted on the gantry. The gantry may be rotatable about a patient region. In some variations, the gantry may have a bore and the patient region located within the bore. The imaging system and the therapeutic radiation system may be located at different gantry angles, but may be located at that same longitudinal location along the gantry bore or patient region (e.g., they may be coplanar). The imaging system may comprise an imaging radiation source and a first multi-leaf collimator disposed in the radiation path of the imaging radiation source. The therapeutic radiation system may comprise a therapeutic radiation source and a second multi-leaf collimator disposed in the radiation path of the therapeutic radiation source. The first and second multi-leaf collimators may be dynamic multi-leaf collimators, and in some variations, may be dynamic binary multi-leaf collimators. The leaf configuration of the multi-leaf collimators may change while the gantry is rotating. In one variation, the first multi-leaf collimator may change leaf configurations at every gantry firing angle to limit the field-of-view of the imaging system to a region of interest where a tumor may be located. The region of interest may include a motion envelope around the tumor. Based on the tumor location data collected from the imaging system, the leaf configuration of the second multi-leaf collimator may be adjusted in order to shape the therapeutic beam to irradiate the tumor, with little or no motion envelope around the tumor. This may help to reduce the radiation exposure of healthy tissue in the vicinity (e.g., adjacent to) of the tumor, while providing an effective radiation dose to the tumor.

One variation of a radiation therapy system may comprise a rotatable gantry, an imaging system mounted on the gantry, a therapeutic radiation source mounted on the gantry, and a controller in communication with the rotatable gantry, the imaging system and the therapeutic radiation system. The imaging system may comprise an imaging radiation source mounted at a first circumferential location along the gantry and a first multi-leaf collimator located in a radiation beam path of the imaging radiation source. The therapeutic radiation system may comprise a therapeutic radiation source mounted at a second circumferential location along the gantry and a second multi-leaf collimator located in a radiation beam path of the therapeutic radiation source. The controller may be configure to set the positions of the leaves of the first multi-leaf collimator to acquire image data of a region-of-interest (ROI) during a treatment session and set the positions of the leaves of the second multi-leaf collimator to apply therapeutic radiation to the ROI during the same treatment session. The rotatable gantry may be configured to rotate at a speed of about 20 RPM or more, or about 60 RPM or more. The leaves of the first multi-leaf collimator may have a first width, the leaves of the second multi-leaf collimator may have a second width, and the first width may be less than the second width. The first circumferential location, second circumferential location and the center of rotation of the gantry may form an angle of about 45 degrees. The positions of the leaves of the first multi-leaf collimator and the positions of the leaves of the second multi-leaf collimator may be set according to pre-loaded image data of the ROI stored in a memory of the controller. The positions of the leaves of the second multi-leaf collimator may be adjusted according to image data acquired by the imaging system. In some variations, the positions of the leaves of the first multi-leaf collimator may define a first radiation-transmitting portion that has an area that is greater than the ROI by a first margin, and the positions of the leaves of the second multi-leaf collimator may define a second radiation-transmitting portion that has an area that is greater than the ROI by a second margin, where the second margin may be smaller than (or the same as) the first margin. The gantry may comprise a plurality of predetermined firing positions around the gantry circumference, and the imaging system may be configured to acquire imaging data while located at a first position. The positions of the leaves of the second multi-leaf collimator may be configured to be adjusted while the gantry is rotating. In some variations, the imaging system may be configured to acquire image data of the ROI at a first firing position before the therapeutic radiation system applies radiation to the ROI from the first firing position. For example, the imaging system may acquire image data of the ROI at a first firing position about 100 ms before the therapeutic radiation system is located at the first firing position. The system may comprise a first detector mounted on the gantry across from the imaging radiation source and a second detected mounted on the gantry across from the therapeutic radiation source. The pre-loaded image data of the ROI may be acquired by cone beam CT. The first and second multi-leaf collimator may be binary collimators. The imaging radiation source may be a kV radiation source and the therapeutic radiation source may be a MV radiation source.

Also described herein is a method for radiation therapy comprising positioning a patient within a patient region of a radiation therapy system comprising a rotatable gantry, an imaging system, a therapeutic radiation system, and a controller. The rotatable gantry may have a first predetermined firing position on a circumference thereof. The imaging system may comprise an imaging radiation source and an imaging system collimator disposed in a radiation beam path of the imaging radiation source. The therapeutic radiation system may comprise a therapeutic radiation source and a therapeutic system collimator disposed in a radiation beam path of the therapeutic radiation source. The controller may comprise a memory containing a first collimator template and a second collimator template. The method may comprise positioning the imaging system at the first firing position, arranging leaves of the imaging system collimator according to the first template, acquiring image data of a patient tumor using radiation from the imaging radiation source that has been shaped by the imaging system collimator, rotating the gantry to position the therapeutic radiation source at the first firing position, modifying the second template according to acquired image data, arranging leaves of the therapeutic system collimator according to the modified second template, and applying therapeutic radiation to the patient tumor using radiation from the therapeutic radiation source that has been shaped by the therapeutic system collimator. In some methods, rotating the gantry and modifying the second template occur simultaneously, and/or modifying the second template and arranging leaves of the therapeutic system collimator occur while the gantry is moving. In some variations, applying therapeutic radiation occurs about 100 ms after acquiring image data. Arranging leaves of the imaging system collimator may comprise positioning the leaves in a pattern that defines a first radiation-transmitting portion shaped according to the first collimator template, and the first radiation-transmitting portion may be sized such that the imaging system irradiates the patient tumor and a first margin around the tumor, the first margin having a first area. In some variations, arranging leaves of the therapeutic system collimator may comprise positioning the leaves in a pattern that defines a second radiation-transmitting portion shaped according to the second collimator template, and the second radiation-transmitting portion may be sized such that the therapeutic radiation system irradiates the patient tumor and a second margin around the tumor, the second margin having a second area smaller than the first area. The first margin may be determined at least in part based on a range of motion of the patient tumor. A location of the second radiation-transmitting portion of the therapeutic system collimator may be shifted based on tumor image data. Alternatively or additionally, a center of gravity of the second radiation-transmitting portion of the therapeutic system collimator may be shifted based on a shift of a center of gravity of the patient tumor. In some variations, the gantry may further comprise a plurality of firing positions located around the circumference of the gantry. The controller memory may contain additional collimator templates, optionally where additional collimator templates may comprise a first set of collimator templates that represent leaf positions of the imaging system collimator at each of the firing positions around the gantry and a second set of collimator templates that represent leaf positions of the therapeutic radiation system collimator at each of the firing positions around the gantry. The first and second sets of collimator templates may be determined based on imaging data of the patient tumor acquired during a pre-treatment imaging session. The tumor may be a lung tumor.

BRIEF DESCRIPTION OF THE DRAWINGS

FIG. 1B depicts a table that outlines the parameters for one variation of a radiation therapy system.

DETAILED DESCRIPTION

Figure 1A:
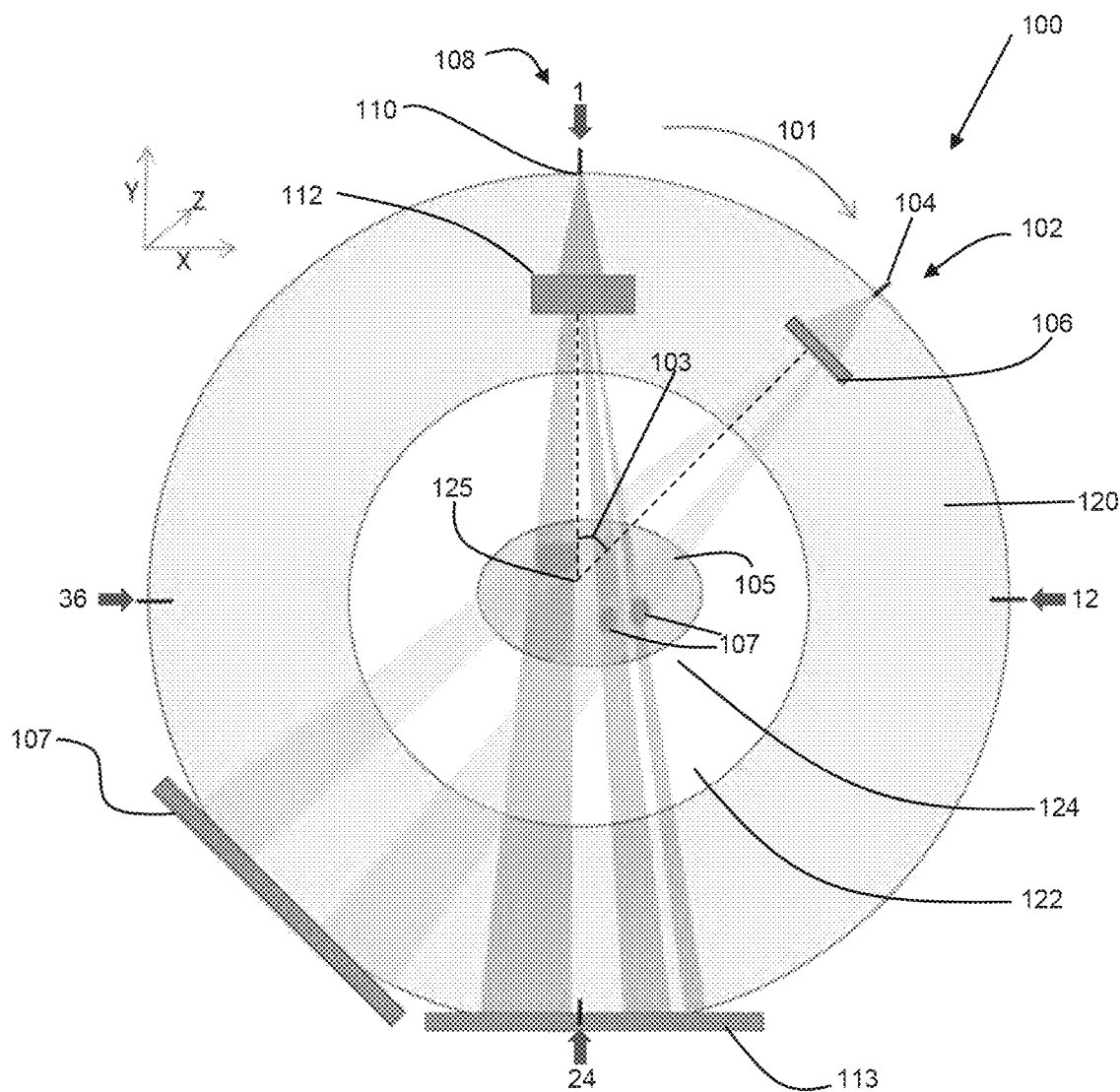
FIG. 1A depicts one variation of a radiation therapy system.

Disclosed herein are systems and methods for real-time tumor motion imaging. The systems and methods described herein may facilitate the acquisition of tumor images during a treatment session that have higher levels of image contrast and quality (e.g., images where the CNR has been increased by about a factor of ten) to provide tumor location data for radiation therapy (e.g., IMRT, IGRT, EGRT). Tumor location data may include tumor centroid data, tumor contour data, tumor motion data (e.g., direction and/or rate of motion), etc. The acquisition of tumor images and/or data may occur in real-time, and/or just prior to the application of a therapeutic radiation beam to the tumor. That is, the latency between the acquisition of tumor image data and the application of radiation to the tumor may be about 10 seconds or less, about 5 seconds or less, about 3 seconds or less, about 2 seconds or less, about 1 second or less, etc., which may allow the system to track tumor location and/or motion.

The systems and methods described herein may be used to acquire tumor location data with or without the use of implanted fiducials. In some variations, a contrast agent may be provided if the ROI is located in a crowded anatomical region, and/or if the boundaries of the ROI are not readily identifiable using the imaging system. Examples of contrast agents may include, but are not limited to, iodine or barium compounds and the like.

System

One variation of a radiation therapy system may comprise a movable gantry, an imaging system mounted on the gantry, and a therapeutic radiation system mounted on the gantry. The system may further comprise a controller in communication with the gantry, imaging system, and the therapeutic radiation system. The therapeutic radiation system may comprise a therapeutic radiation source, for example, an MV radiation source (e.g., linac), and/or a proton beam source. The therapeutic radiation system may further comprise a multi-leaf collimator disposed over the therapeutic radiation source and/or in the beam path of the therapeutic radiation source and a therapeutic radiation detector located opposite the therapeutic radiation source. The imaging system may comprise an imaging radiation source, such as a kV X-ray source, a dynamic multi-leaf collimator disposed over the imaging radiation source and/or in the beam path of the imaging radiation source, and a detector located opposite the imaging radiation source. Alternatively or additionally, the imaging system may comprise a PET system, and/or a MRI system, and/or a cone beam CT system.

Gantry

The gantry may comprise a circular or ring gantry (e.g., closed bore ring gantry, open bore ring gantry), and/or may comprise one or more arms (e.g., C-arm gantry). The system may comprise a motion system coupled to the gantry to move the imaging system and/or the therapeutic radiation system about a patient area. In some variations, a motion system may rotate the gantry such that one or both of the imaging system and the therapeutic radiation system may rotate around a patient area, and/or a motion system may translate the gantry such that one or both of the imaging and therapeutic radiation systems may move along a longitudinal length of the patient area, e.g., along an axis that is transverse or perpendicular to a plane of gantry rotation. In some variations, the motion system may drive the gantry in order to position the imaging system and the therapeutic radiation system to various pre-defined locations about the patient area. These pre-defined locations may be referred to as firing positions or firing angles. Firing positions or firing angles may be identified by indices, and/or, in the case of a rotatable gantry, rotational angle around the patient area and/or location along the circumference of the gantry. A motion system may be configured to move the imaging system and/or the therapeutic radiation system from one firing position to an adjacent firing position in less than about 0.4-0.1 seconds. The position and motion of the imaging system and the therapeutic radiation system may be controlled separately/independently (e.g., such that positioning or moving the imaging system does not necessarily position or move the therapeutic radiation system) by using, for example, two motion systems. Alternatively, position and motion of the imaging system and the therapeutic radiation system may be controlled together (e.g., such that positioning or moving the imaging system positions or moves the therapeutic radiation system in a corresponding fashion) by using, for example, a single motion system or two motion systems that are controlled in synchrony. In some variations, the radiation therapy system may comprise a first ring gantry and a second ring gantry, where the imaging system is located on the first ring gantry and the therapeutic radiation source is located on the second ring gantry. The first and second ring gantries may be concentric (i.e., the second ring gantry is nested within the first ring gantry), or the first ring gantry and the second ring gantry may be located adjacent to each other. The first and second ring gantries may be controlled by a single motion system, or may each have their own independently controllable motion systems. Any suitable type of gantry motion systems may be used, for example, motion systems for circular gantries may comprise a slip ring and a drive train that contacts and rotates the slip ring.

In some variations, the radiation therapy system gantry may comprise a first arm and a second arm, where the imaging system is mounted on the first arm and the therapeutic radiation system is mounted on the second arm. For example, a radiation therapy system may comprise a first pair of arms located opposite each other, where an imaging radiation source is mounted on one of the arms and an imaging radiation detector is mounted on the other of the arms. The radiation therapy system may comprise a second pair of arms located opposite each other, where a therapeutic radiation source is mounted on one of the arms and a therapeutic radiation detector is mounted on the other of the arms. In some variations, gantry may comprise a rotatable frame and one or more arms extending from the frame. The one or more arms may be curved, and may be C-shaped. The rotation of the frame and/or arm(s) may be provided by one or more motion systems. Motion systems for gantries having one or more arms may comprise a slip ring and drive train, or any other suitable motion system.

The therapeutic radiation system and the imaging system may be arranged on the gantry such that the field-of-view of the imaging system is in-plane with the radiation beam from the therapeutic radiation source. In some variations, the imaging system and the therapeutic radiation source may be mounted on the gantry such that they are coplanar with each other (i.e., on the same cross-sectional plane that is transverse to the longitudinal axis of the gantry patient area). That is, the central axis of the therapeutic radiation beam may be coplanar with the central axis of the field-of-view of the imaging system. For example, the gantry may be a circular or ring gantry with a longitudinal length, and the imaging system and the therapeutic radiation source may be located at the same longitudinal location along the length of the gantry, or in other words, may be located on the same cross-sectional plane or slice of the gantry (e.g., cross-sectional plane that is transverse to the longitudinal axis of the gantry).

Multi-Leaf Collimator

In some variations where the imaging system comprises a kV radiation source and the therapeutic radiation system comprises an MV radiation source, each system may comprise a multi-leaf collimator (MLC) disposed over each of their radiation sources. The MLC may be any type of dynamic multi-leaf collimator (DMLC), as may be desirable, for example, a 2-D conformal MLC or binary collimator, where the configuration of the leaves can be adjusted during a treatment session (e.g., in real-time, using an actuation mechanism that moves the leaves without manual manipulation of the MLC by a user). The leaves of the DMLC may be configured to change their position while the gantry is moving between firing angles so that each of the leaves is at a specified location when the respective system is located at a particular firing angle. The positions of the leaves of a MLC at a particular firing angle or position may be referred to as a MLC template. The shape of each template resembles the projected image of tumor shape from that particular angle. An MLC template may specify the position of each and every leaf in the MLC such that leaf pattern corresponds with a desired radiation beam pattern or shape. For example, a MLC template may be set of instructions that indicate the position of each leaf of the MLC (e.g., displacement along a leaf travel path, displacement from the edge of the radiation beam path, etc.). A different MLC template may be computed for each firing angle so that a radiation beam emitted at that firing angle is shaped to correspond with a projection of the tumor at that firing angle. In some variations, an MLC template may specify the position of each leaf such that the pattern (e.g., shape and location) of the opening(s) in the MLC (i.e., the radiation-transmitting portion of the MLC) correspond with the desired radiation beam pattern. As will be described further below, in some variations, an MLC template at a particular firing angle may form a pattern such that the radiation beam at that firing angle has a shape that corresponds with the projection of a tumor region on that firing angle. An MLC template may also provide for a beam shape that corresponds to the size and shape of a tumor, plus a margin around the tumor. For example, the additional margin around the tumor may correspond with a motion envelope, and/or may be a region around the tumor that is selected to help ensure that tumor area (which may include the tumor boundaries) are irradiated. The size of the margin around a tumor may correspond to the expected or predicted range of motion of the tumor. A set of MLC templates may comprise a plurality of MLC templates for a plurality of firing positions or angles around the patient area. CT or cone beam CT image data set collected prior to treatment may be used by the controller to generate a set of kV-DMLC templates and/or MV-DMLC templates. These templates may be created by digitally reconstructed radiographs.

The DMLCs for a kV radiation source and/or a MV therapeutic radiation source may help to reduce the radiation exposure of a patient during an imaging and/or treatment session by limiting and/or shaping the kV and MV radiation beams to only the ROI(s) and/or tumor(s) (including, in some examples, a tumor movement margin around the tumor). In particular, the kV DMLC may be used to limit the patient region exposed to kV radiation by shaping the kV radiation beam to regions where a tumor may be located. The leaf configurations of the kV DMLC may be determined at least in part by images of tumor regions, which may be acquired using any desirable imaging modality, and/or may be acquired in a diagnostic imaging session or a treatment planning session. That is, instead of irradiating a patient with the full kV radiation beam (e.g., using a system that does not have a DMLC disposed in front of the kV radiation source, or opening all of the leaves of an MLC), the kV radiation beam is shaped and/or limited to only to regions that have been determined to have a tumor and/or regions that may encompass a moving tumor. This may help to significantly reduce the dose to the healthy tissue from kV imaging Additionally, because the irradiation of kV radiation for imaging is more targeted (i.e., has a narrower field of view or "keyhole" field of view), a higher dose may be used as compared to the wide-field or full-field irradiation that is typically used for soft tissue imaging. Shaping or limiting the kV radiation beam using the kV DMLC may also help to reduce scattered X-rays from the patient to the kV detector. Since scatter is a major factor for poor image quality, reducing scatter may facilitate the generation of a better-quality image data. For example, a tumor having a dimension of about 3 cm may be imaged with a 5×5 cm DMLC field of view (FOV). That is, the kV DMLC leaf configuration may be adjusted to shape the kV radiation beam to have a 5×5 cm irradiation field. In contrast, to image a 3 cm tumor, a conventional fixed collimator may irradiate 40×40 cm FOV, and expose the patient to significantly more radiation (e.g., the dose-area product without a kV DMLC may be greater than the dose-area product with a kV DMLC by a factor of 64). The noise from the scattered X-rays may be reduced, to the first order, approximately by square-root of the dose-area product (that is, by a factor of about 8). This may result in a significant image quality improvement, for example, by increasing the CNR by a factor of about 8 or more. Because a smaller irradiation area or FOV allows for increased X-ray exposure with reduced scatter, tumors that may not be visible in conventional X-ray fluoroscopy may now visible and may be tracked in real-time. Alternatively or additionally, the kV imaging system may be operated in cone beam computed tomography mode (CBCT) where all of the leaves of the kV DMLC are open (i.e., not obstructing the kV radiation beam path). A kV imaging system may comprise a jaw collimator that may be used to collimate the slice width along the Z-direction (FIG. 1A).

In some variations, the set of MV-DMLC templates comprising a kV-DMLC template for each firing position around a patient region may correspond with (e.g., similar or identical to) the set of kV-DMLC templates. Alternatively, the set of MV-DMLC templates may provide a beam shape that corresponds in size and shape with the beam shape provided by the set of kV-DMLC templates, but the location of the beam may be shifted. For example, if image data collected using the kV-DMLC templates indicates that a tumor has moved or shifted, the MV-DMLC templates may be updated to reflect that movement or shift. If the size and shape of the tumor, as detected using the kV-DMLC templates, has not changed, the size and shape of the beam provided by the MV-DMLC templates may not change.

Controller

The controller may comprise a processor and a machine-readable memory that stores data relating to the operation of the imaging system, therapeutic radiation system, and gantry motion system(s), for example, treatment plans, image data, dose data, system control signals and/or commands, etc. The processor may perform computations based on the imaging data, and may generate signals and/or commands to adjust the operation of the radiation therapy system according to image data computations. The controller may comprise one or more processors and one or more machine-readable memories in communication with the one or more processors. The controller may be connected to the imaging system, therapeutic radiation system, and/or gantry motion system(s) by wired or wireless communication channels. The controller may be located in the same or different room as the patient. In some variations, the controller may be coupled to a patient platform or disposed on a trolley or medical cart adjacent to the patient and/or operator.

The controller may be implemented consistent with numerous general purpose or special purpose computing systems or configurations. Various exemplary computing systems, environments, and/or configurations that may be suitable for use with the systems and devices disclosed herein may include, but are not limited to software or other components within or embodied on personal computing devices, network appliances, servers or server computing devices such as routing/connectivity components, portable (e.g., hand-held) or laptop devices, multiprocessor systems, microprocessor-based systems, and distributed computing networks.

Examples of portable computing devices include smartphones, personal digital assistants (PDAs), cell phones, tablet PCs, phablets (personal computing devices that are larger than a smartphone, but smaller than a tablet), wearable computers taking the form of smartwatches, portable music devices, and the like, and portable or wearable augmented reality devices that interface with an operator's environment through sensors and may use head-mounted displays for visualization, eye gaze tracking, and user input.

In some embodiments, a processor may be any suitable processing device configured to run and/or execute a set of instructions or code and may include one or more data processors, image processors, graphics processing units, physics processing units, digital signal processors, and/or central processing units. The processor may be, for example, a general purpose processor, Field Programmable Gate Array (FPGA), an Application Specific Integrated Circuit (ASIC), or the like. The processor may be configured to run and/or execute application processes and/or other modules, processes and/or functions associated with the system and/or a network associated therewith (not shown). The underlying device technologies may be provided in a variety of component types, e.g., metal-oxide semiconductor field-effect transistor (MOSFET) technologies like complementary metal-oxide semiconductor (CMOS), bipolar technologies like emitter-coupled logic (ECL), polymer technologies (e.g., silicon-conjugated polymer and metal-conjugated polymer-metal structures), mixed analog and digital, or the like.

In some embodiments, memory may include a database (not shown) and may be, for example, a random access memory (RAM), a memory buffer, a hard drive, an erasable programmable read-only memory (EPROM), an electrically erasable read-only memory (EEPROM), a read-only memory (ROM), Flash memory, etc. The memory may store instructions to cause the processor to execute modules, processes and/or functions associated with kV image acquisition, image processing (e.g., background subtraction, tumor contour enhancements, diagnostic image enhancements), DMLC template computations (e.g., kV-DMLC templates and/or MV-DMLC templates), gantry motion and positioning, therapeutic radiation source activation (e.g., pulse timing), etc.

Some embodiments described herein relate to a computer storage product with a non-transitory computer-readable medium (also may be referred to as a non-transitory processor-readable medium) having instructions or computer code thereon for performing various computer-implemented operations. The computer-readable medium (or processor-readable medium) is non-transitory in the sense that it does not include transitory propagating signals per se (e.g., a propagating electromagnetic wave carrying information on a transmission medium such as space or a cable). The media and computer code (also may be referred to as code or algorithm) may be those designed and constructed for the specific purpose or purposes. Examples of non-transitory computer-readable media include, but are not limited to, magnetic storage media such as hard disks, floppy disks, and magnetic tape; optical storage media such as Compact Disc/Digital Video Discs (CD/DVDs); Compact Disc-Read Only Memories (CD-ROMs), and holographic devices; magneto-optical storage media such as optical disks; solid state storage devices such as a solid state drive (SSD) and a solid state hybrid drive (SSHD); carrier wave signal processing modules; and hardware devices that are specially configured to store and execute program code, such as Application-Specific Integrated Circuits (ASICs), Programmable Logic Devices (PLDs), Read-Only Memory (ROM), and Random-Access Memory (RAM) devices. Other embodiments described herein relate to a computer program product, which may include, for example, the instructions and/or computer code disclosed herein.

In some embodiments, the systems and methods may be in communication with other computing devices via, for example, one or more networks, each of which may be any type of network (e.g., wired network, wireless network). A wireless network may refer to any type of digital network that is not connected by cables of any kind. Examples of wireless communication in a wireless network include, but are not limited to cellular, radio, satellite, and microwave communication. However, a wireless network may connect to a wired network in order to interface with the Internet, other carrier voice and data networks, business networks, and personal networks. A wired network is typically carried over copper twisted pair, coaxial cable and/or fiber optic cables. There are many different types of wired networks including wide area networks (WAN), metropolitan area networks (MAN), local area networks (LAN), Internet area networks (IAN), campus area networks (CAN), global area networks (GAN), like the Internet, and virtual private networks (VPN). Hereinafter, network refers to any combination of wireless, wired, public and private data networks that are typically interconnected through the Internet, to provide a unified networking and information access system.

Cellular communication may encompass technologies such as GSM, PCS, CDMA or GPRS, W-CDMA, EDGE or CDMA2000, LTE, WiMAX, and 5G networking standards. Some wireless network deployments combine networks from multiple cellular networks or use a mix of cellular, Wi-Fi, and satellite communication. In some embodiments, the systems, apparatuses, and methods described herein may include a radiofrequency receiver, transmitter, and/or optical (e.g., infrared) receiver and transmitter to communicate with one or more devices and/or networks.

Any of the methods described herein may be performed by software (executed on hardware), hardware, or a combination thereof. Hardware modules may include, for example, a general-purpose processor (or microprocessor or microcontroller), a field programmable gate array (FPGA), and/or an application specific integrated circuit (ASIC). Software modules (executed on hardware) may be expressed in a variety of software languages (e.g., computer code), including C, C++, Java®, Python, Ruby, Visual Basic®, and/or other object-oriented, procedural, or other programming language and development tools. Examples of computer code include, but are not limited to, micro-code or micro-instructions, machine instructions, such as produced by a compiler, code used to produce a web service, and files containing higher-level instructions that are executed by a computer using an interpreter. Additional examples of computer code include, but are not limited to, control signals, encrypted code, and compressed code.

In some instances, aspects of the innovations herein may be achieved via logic and/or logic instructions including program modules, executed in association with such components or circuitry, for example. In general, program modules may include routines, programs, objects, components, data structures, etc. that perform particular tasks or implement particular instructions herein. The inventions may also be practiced in the context of distributed circuit settings where circuitry is connected via communication buses, circuitry or links. In distributed settings, control/instructions may occur from both local and remote computer storage media including memory storage devices.

One variation of a radiation therapy system configured for real-time tumor tracking and treatment is depicted and described in FIGS. 1A-1B. FIG. 1A depicts one variation of a radiation therapy system comprising an MV radiation therapy system, a kV X-ray imaging system for real-time tumor tracking, and a fast rotating ring gantry (e.g., from about 50 RPM to about 70 RPM, about 60 RPM, about 70 RPM). Both the MV therapeutic radiation system and the kV imaging system are mounted on the fast rotating gantry and each system comprises a dynamic MLC. A dynamic MLC may be configured to changed leaf configurations during a treatment session and/or may be capable of changing from one leaf configuration to another leaf configuration in approximately the time it takes for the gantry to rotate from one firing position to the next firing position (e.g., an adjacent firing position). Both systems may comprise high-speed, real-time image detectors. The kV system may acquire tumor location data from a particular firing position or viewing angle, and a short time after the acquisition of the tumor location data, the MV therapeutic radiation system may emit radiation beams at the tumors from the same firing position or viewing angle. In one variation, radiation therapy system 100 may comprise an imaging system 102 comprising an imaging radiation source (e.g., a kV X-ray source such as a high-power kV X-ray source) 104 and a collimator 106 disposed over the kV X-ray source, a therapeutic radiation system 110 comprising a therapeutic radiation source (e.g., an MV X-ray source such as a linac) 110 and a collimator 112 disposed over the MV X-ray source, and a rotatable gantry 120, upon which the imaging system 102 and the therapeutic radiation system 110 are mounted. The imaging system may further comprise a kV detector 107 (e.g., a dynamic kV detector) located opposite the kV X-ray source 104, and the therapeutic radiation system may further comprise an MV detector 113 (e.g., a dynamic MV detector) located opposite the MV X-ray source 110. In this variation, the gantry 120 is a ring (e.g., circular) gantry, however, it may have any of the gantry geometries and configurations described above.

Circular Gantry

The gantry 120 may comprise a longitudinal bore 122, and a patient area 124 may be located within the bore 122. A patient 105 may have one or more tumor regions 107, and may be located within the patient area 124 of the bore 122. The patient 105 may be mounted on a movable patient platform (not shown) that may be configured to move the patient in a longitudinal direction such that the tumor regions sequentially cross the radiation beam of the kV radiation source and/or MV radiation source (e.g., if the circular gantry rotates in the X-Z plane, the patient platform may move along the Y axis). In some variations, the patient platform may be able to pivot, tilt, or otherwise rotate (e.g., roll, pitch, yaw) to position the patient and may have, for example, four or more degrees of freedom. The gantry 120 may be closed bore gantry (i.e., where at least one end of the gantry is enclosed) or may be an open bore gantry (i.e., where both ends of the gantry are enclosed). The gantry 120 may be rotatable such that the imaging system and the therapeutic radiation system may be moved around the patient area 124. The gantry 120 may rotate at a rate of about 10 RPM to about 70 RPM (e.g., about 60 RPM), and may rotate clockwise as indicated by arrow 101 or may rotate counter-clockwise. The radiation therapy system may comprise a plurality of pre-defined firing positions around the patient area 124, and the gantry 120 may be configured to move to each of those firing positions during an imaging and/or treatment session. A radiation therapy system may have any number of firing positions that may be distributed around the patient area, for example, about 10 firing positions, about 25 firing positions, about 35 firing positions, about 36 firing positions, about 50 firing positions, about 64 firing positions, about 100 firing positions, about 128 firing positions about 150 firing positions, etc. The radiation therapy system 100 may comprise 48 firing positions (e.g., firing positions 1, 12, 24, and 36 are represented by arrows in FIG. 1A), which may be distributed evenly around the patient area 124 (i.e., about 7.5 degrees between each firing position). In other variations, firing positions may not be distributed evenly around the patient area, as may be desirable. The locations of the kV detector and the MV detector allow for the measurement of radiation from the kV and MV X-ray sources, respectively, after they have crossed the patient area and/or interacted with a patient. The radiation therapy system 100 may also comprise a patient platform (not shown) that is moveable within the bore 122 of the gantry 120, to laterally translate the patient along the longitudinal axis of the bore. In some variations, the patient platform may have six or more degrees of freedom (e.g., forward, backward, right, left, roll, pitch, yaw), and its position and orientation with respect to the kV X-ray source and/or MV X-ray source may be adjusted in accordance with the real-time position of the patient and/or the one or more tumor regions.

As depicted in FIG. 1A, the imaging system 102 and the therapeutic radiation system 108 are arranged such that the radiation beams from the kV X-ray source 104 and the MV X-ray source 110 are coplanar with each other. That is, the kV X-ray source and the MV X-ray source may be located on the same cross-sectional plane of the gantry (e.g., the kV and MV X-rays source may be coplanar with each other). In some variations, the kV imaging system and the MV therapeutic radiation system are in the same X-Y plane, and/or may be fixed to and rotate with the gantry. The kV X-ray source and the MV X-ray source may be circumferentially offset from each other, located at different angles around the central axis 125 (e.g., axis of rotation) of the gantry 120

(e.g., angular separation). For example, the location of the kV X-ray source, center of the central axis 125, and the location of the MV X-ray source may form an angle (e.g., central angle 103) from about 10 degrees to about 170 degrees, e.g., about 30 degrees, about 45 degrees, about 60 degrees, about 90 degrees, about 120 degrees, about 135 degrees, etc. The central angle between the kV X-ray source and the MV X-ray source may be determined at least in part by the field-of-view (FOV) size along the x-axis, and/or number of firing positions around the gantry, and/or rotational speed of the gantry, image acquisition rate of the kV and the MV detectors, data processing rate of the controller, etc. The angular separation between the kV and MV X-ray sources may be at least partially determined based on the physical sizes and geometry of the MV and kV X-ray sources. For example, the angular separation may be less for kV and MV X-ray sources that have a relatively compact footprint as compared to the angular separation for kV and MV X-rays sources that have a larger footprint. The angular separation may optionally be dependent on the spacing between firing positions around the gantry, and may optionally dependent on the amount of kV image processing time needed before the MV X-ray source arrives at that firing position. For example, the angular separation may be selected to attain a desired latency between imaging acquisition by the kV imaging system and irradiation by the MV therapeutic radiation system. That is, for a given desired latency, the angular separation may be greater for a faster rotating gantry than for a slower rotating gantry. In some variations, the MV X-ray source may be a certain number of firing positions away from the kV X-ray source. For example, the location of the MV X-ray source may be 3, 4, 5, 6, 7, 8, 9, 10, 12, 15, 16, 20, 25, etc. firing positions away from the kV X-ray source. In a variation where the gantry is rotatable, the gantry may rotate in a direction where the FOV of the imaging system sweeps a portion of the patient area before the therapeutic radiation system applies radiation to that portion. For example, the gantry may be rotatable in a direction where the therapeutic radiation system follows the imaging system. That is, the kV imaging system may be "ahead" of the MV system in the rotating direction separated by the central angle (e.g., about 45 degrees). By rotating the gantry in this fashion, the imaging system may acquire imaging data of a patient region from a particular gantry angle (i.e., firing position or angle) before the therapeutic radiation system arrives at that gantry angle. Imaging data acquired by the imaging system (which may comprise tumor location data, tumor geometry data, tumor and/or patient movement data, etc.) at a particular gantry angle may be used to shape and/or direct radiation generated by the therapeutic radiation system when it arrives at that gantry angle a short time after the imaging system. Further details regarding the operation and timing of the radiation therapy system 100 are provided below.

kV DMLC and MV DMLC

The imaging system may comprise a multi-leaf collimator disposed over the kV radiation source, in the kV radiation beam path. Similarly, the therapeutic radiation system may comprise a multi-leaf collimator disposed over the MV radiation source, in the MV radiation beam path. The multi-leaf collimator (MLCs) for one or both of the imaging system and the therapeutic radiation systems may be a dynamic MLC. A dynamic MLC (DMLC) is one that is configured to change its leaf configurations during a treatment session, for example, while the gantry is moving or rotating, and/or while the radiation source is activated or turned on. In some variations, the DMLC for one or both of the imaging system and the radiation therapy system may be configured to change leaf configurations within the time it takes for the gantry to rotate from one firing position to the next firing position (e.g., the adjacent firing position). For example, the gantry may be configured to rotate at a speed from about 10 RPM to about 70 RPM, e.g., about 30 RPM to about 70 RPM, about 60 RPM, and the DMLC for the imaging system and the therapeutic radiation system may be configured to move a collimator leaf from a closed position (i.e., blocking radiation beam along the travel path of the leaf) to a fully open position (i.e., no obstruction of the radiation beam along the travel path of the leaf) in about 10 ms to about 25 ms, e.g., about 12 ms, about 15 ms, about 16.7 ms, about 20 ms, about 23 ms. The kV DMLC 106 may be similar to MV DMLC 112 in geometry and design. In some variations, the thickness of the leaves (e.g., the dimension of a leaf that is along the radiation beam path) of the kV DMLC may be less than the thickness of the leaves of the MV DMLC. For example, the leaves of the DMLC may comprise one or more high attenuation metals, e.g., tungsten and the like. The leaf thickness (i.e., the leaf dimension along the beam path) may vary in accordance with the energy of the radiation source. For example, the leaf thickness of a MV X-ray source DMLC may be from about 6 cm to about 10 cm, and/or the leaf thickness of a kV X-ray source DMLC may be from about 3 mm to about 5 mm. The kV DMLC 106 and the MV DMLC 112 may have the same or different number of leaves, and may each have, for example, 12, 24, 25, 36, 48, 50, 60, 64, 75, 85, 100 leaves. In some variations, the kV DMLC and the MV DMLC may be binary multi-leaf collimators (e.g., leaves movable between two states: open and closed) and/or may be two dimensional multi-leaf collimators (e.g., leaves movable between open and closed states, but also able to be retained at a position between the open and closed states). The leaf actuation mechanisms for the kV DMLC and/or the MV DMLC may be any suitable mechanism, for example, pneumatic actuation mechanisms, cam-based actuation mechanisms, and/or any of the mechanisms described in U.S. patent application Ser. No. 15/179,823, filed Jun. 10, 2016, which is hereby incorporated by reference in its entirety.

FIG. 1B depicts a table that summarizes example of parameters of a radiation therapy system, such as the radiation therapy system of FIG. 1A, along with exemplary operating conditions or parameters. The gantry 120 may be configured to rotate at a speed of about 1 second per revolution (e.g., about 60 RPM). With 48 firing positions located at about 7.4 degrees apart from each, and the central angle between the kV system and the MV system of about 45, degrees, the time interval (e.g., lag time) between image acquisition by the kV imaging system and firing therapeutic radiation by the MV therapeutic radiation system may be about 0.1 second. In situations where a tumor moves at a speed of about 1 cm/s (e.g., a lung tumor), this may allow the radiation therapy system to track tumors within about a 1 mm range. Any gantry capable of rotating at a speed of about 60 RPM may be used, such as the gantry described in U.S. patent application Ser. No. 15/814,222, filed Nov. 15, 2017, which is hereby incorporated by reference in its entirety.

C-Arm Gantry

Figure 1C:
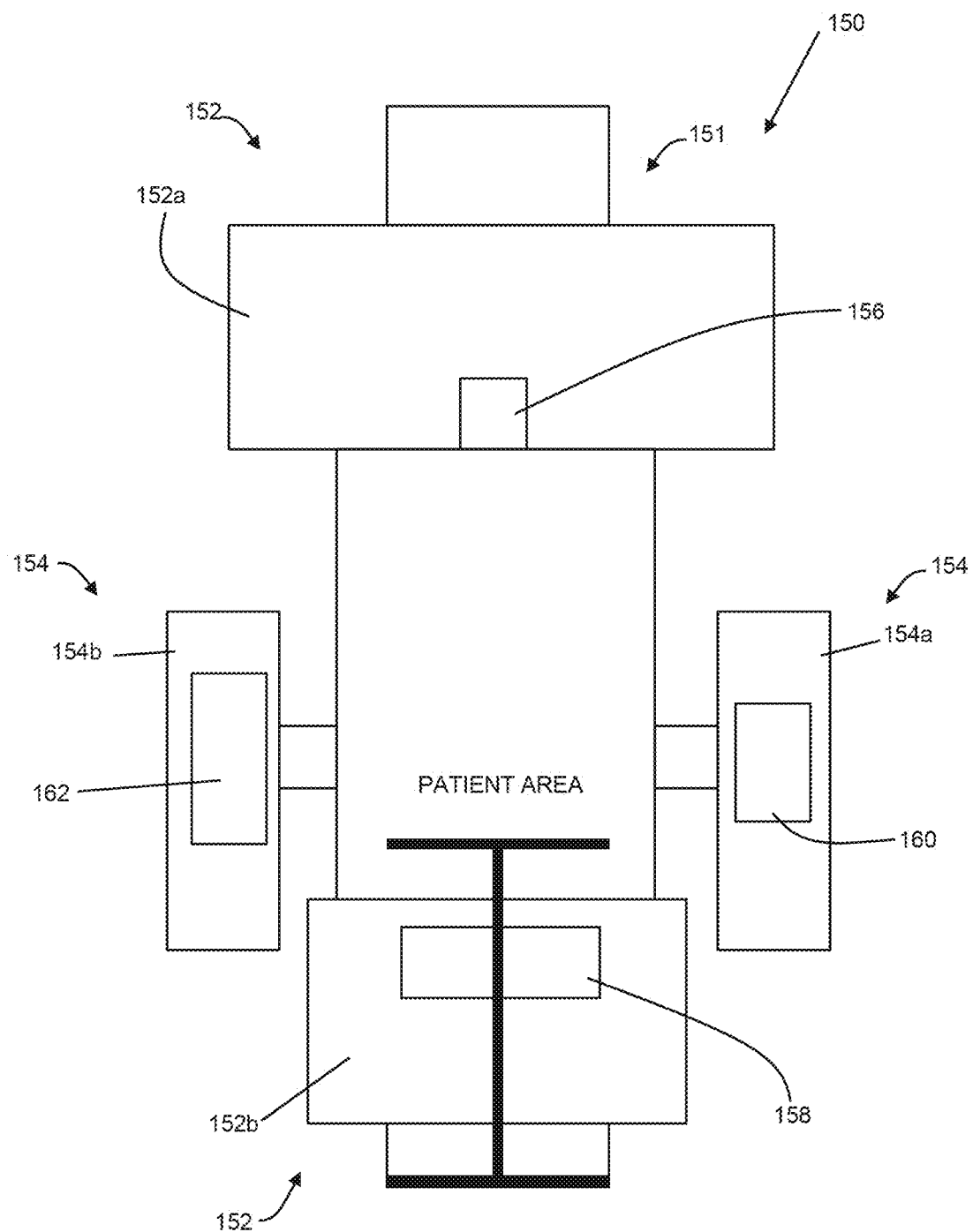
FIG. 1C depicts another variation of a radiation therapy system.

While a circular or ring-shaped gantry (which may or may not be continuously rotating) is depicted and described in FIGS. 1A-1B, it should be understood that other variations of radiation therapy systems may be configured for real-time tumor tracking and treatment. Another variation of a radiation therapy system is depicted in FIG. 1C. Radiation therapy system 150 may comprise a gantry 151 comprising a first pair of arms 152 rotatable about a patient area and a second pair of arms 154 rotatable about the patient area, an imaging system comprising a kV radiation source 156 mounted on a first arm 152a of the first pair of arms 15 and a kV detector 158 mounted on a second arm 152b of the first pair of arms 152, and a therapeutic radiation system comprising an MV radiation source 160 mounted on a first arm 154a of the second pair of arms 154 and an MV detector 162 mounted on a second arm 154b of the second pair of arms 154. The first and second arms of the first pair of arms 152 may be located opposite each other (e.g., on opposite sides of the patient area, across from each other, and/or about 180 degrees from each other), such that the kV radiation source 156 and the kV detector 158 are located opposite each other (e.g., the kV detector is located in the beam path of the kV radiation source). The first and second arms of the second pair of arms 154 may be located opposite each other (e.g., on opposite sides of the patient area, across from each other, and/or about 180 degrees from each other), such that the MV radiation source 160 and the MV detector 162 are located opposite each other (e.g., the MV detector is located in the beam path of the MV radiation source). The first pair of arms and the second pair of arms may be radially offset from each other, for example, from about 10 degrees to about 170 degrees (e.g., about 15 degrees, about 25 degrees, about 30 degrees, about 45 degrees, about 90 degrees, about 100 degrees, about 120 degrees, about 150 degrees, etc.) offset from each other. That is, if the arms of the first pair of arms are located at positions (e.g., firing angles or positions) 0 degrees and 180 degrees around a patient area, in some variations, the arms of the second pair of arms may be located at 90 degrees and 270 degrees. In other variations, the arms of the second pair of arms may be located at 10 degrees and 190 degrees, at 30 degrees and 210 degrees, at 45 degrees and 225 degrees, at 100 degrees and 280 degrees, etc., or any other offset.

Figure 2A:
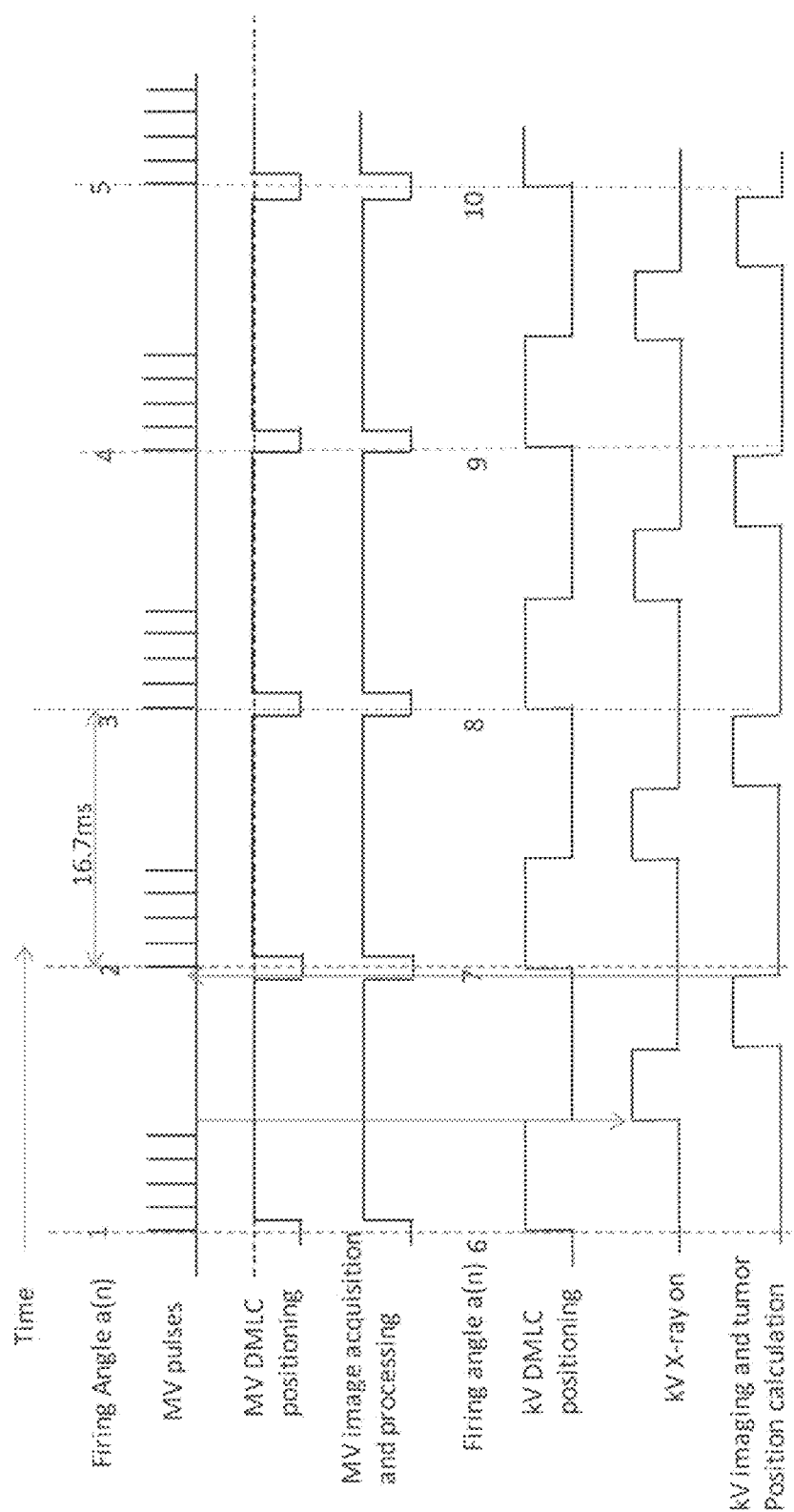
FIG. 2A depicts one variation of a system operation timing diagram.

FIG. 2A depicts one variation of a timing diagram representing the operation of kV imaging system and the MV therapeutic radiation systems depicted in FIGS. 1A-1C during a treatment session. As the gantry rotates, the imaging system stops at different firing positions or angles (e.g., firing angle a(n) 1, 2, 3, 4, 5, 6, 7, 8, 9, 10). In this example, the kV imaging system is six firing positions or angles ahead of the therapeutic radiation system. That is, when the kV imaging system is at firing position 6 (i.e., after having passed through firing positions 1, 2, 3, 4, and 5), the therapeutic radiation system is at firing position 1. For a gantry rotating at a speed of about 60 RPM, the therapeutic radiation system arrives at a particular firing position about 100 ms after the imaging system. In the example depicted in FIG. 2A, when the imaging system is at firing angle a(n)=6 (i.e., the imaging system having been at firing angle a(n)=1 about 100 ms prior), the therapeutic radiation system is at firing angle a(n)=1. While at firing angle a(n)=1, the therapeutic radiation therapy system activates the MV radiation source and applies, for example, six radiation pulses. At the time of the first pulse, the leaves of the MV DMLC may not be moving (signal value low or zero), but may move to a different configuration by the time the second to sixth pulses are applied. Alternatively, the leaves of the MLC may be stationary while the radiation pulses are applied. The leaf configuration of the MV DMLC (e.g., MV-DMLC template) during the first pulse and/or successive pulses may be based on, for example, treatment plans developed in advance of the treatment session and/or the kV image data collected about 100 ms prior (e.g., about 6 firing angles prior). MV image data may be collected during the pulse intervals. At firing angle a(n)=6, the leaves of the kV DMLC of the imaging system may be moving to a leaf configuration, for example, a leaf configuration (e.g., a kV-DMLC template) based on treatment plans developed in advance of the treatment session. While the kV DMLC is changing leaf configurations to attain a certain kV-DMLC template at firing angle a(n)=6, the kV X-ray source may not be turned on. After the leaves have completed their motion to the desired kV-DMLC template, the kV X-ray source may then be turned on or activated. The kV detector may be in image data detection mode before and/or during the activation of the kV X-ray source, and may be in image data computation mode for a selected time period after the kV X-ray source has been de-activated. The MV DMLC positioning may be move-and-stop type, shown in solid line, or can be a continuous move type, shown in dashed line. As indicated by the two vertical arrows, the kV and the MV pulses can be interleafed to avoid cross-talk and scatter X-ray from MV to kV imaging. The kV DMLC may be move-and-stop, where kV X-ray beams are applied only during the DMLC stop. The imaging system may acquire kV image data at every firing position prior to the arrival of the therapeutic radiation system at each firing position, as depicted in FIG. 2A. In some variations, the therapeutic radiation system may be configured to apply radiation from a particular firing position only if kV image data was acquired that confirms the size, shape, and location of the tumor from that firing position. Alternatively, kV image data may not be acquired at every firing position, but may be acquired at a subset of firing positions, such as the firing positions where a tumor is expected.

The image data computation may comprise using the collected image data to generate new MV-DMLC templates and/or update existing MV-DMLC templates for firing position a(n)=6. Further details regarding some variations of methods for generating kV-DMLC templates, MV-DMLC templates, and tracking tumor motion using kV image data will be provided below.

Methods

The geometry (e.g., size and shape) and/or location of a tumor may be measured at various times before, during and after a treatment session. In some variations, image data may be acquired before treatment, for example, during a treatment planning or diagnostic imaging session. Treatment planning and/or diagnostic imaging may take place days, weeks, or months before a treatment session. Image data collected during such sessions may include the size, shape, and/or number of tumors, and may optionally include information about the motion of tumors (e.g., motion envelope of moving tumors). While the methods described below may refer to one or two tumors, it should be understood that these methods may be applied to any number of tumors. In some variations, the image data may comprise motion-averaged cross-sectional images. A controller may store this pre-treatment image data and may use this data to compute the multi-leaf collimator leaf positions at each firing angle or position for imaging and/or treatment. For example, kV-CBCT imaging data (e.g., CBCT images) may be used by the controller to create a set of kV-DMLC and/or MV-DMLC templates. The kV-DMLC templates may be used to position the leaves of the kV DMLC to shape the kV beam to correspond with the geometry and location of the tumor, which may help limit patient radiation exposure while imaging the patient during a treatment session (e.g., for real-time tumor-tracking).

In some variations, the kV-DMLC templates may be used in an additional (optional) pre-treatment imaging session (e.g., days before and/or minutes before a treatment session). For example, the kV-DMLC templates computed based on an earlier imaging session (e.g., a treatment planning or diagnostic imaging session, as described above) may be used to collect kV image data of the patient and/or tumor(s) from all firing angles or positions. That is, the gantry may rotate the kV imaging system to each of the firing angles, the leaves of the kV DMLC may be positioned in accordance with the kV-DMLC template generated for that firing angle, a kV radiation beam may be applied to the patient, and the kV imaging data acquired by the kV detector. The acquired kV image data may comprise background and/or anatomical imaging data from all firing angles or positions, and in some variations, may comprise a set of tumor images without a motion envelope. In some variations, this kV image data may be used to create a set of templates for the MV DMLC. Alternatively or additionally, kV image data may be used to generate a set of background images of non-moving and bony anatomies for each all firing angles or positions.

The geometry and location of a tumor (and optionally, the region surrounding the tumor) or any ROI may be measured during a treatment session. In one variation of a method, the kV imaging system may continuously acquire image data of a tumor (and/or surrounding tumor region and/or any ROI) identified in the previous imaging sessions at each firing angle during a treatment session. For example, the kV detector may measure projection data of the tumor at each firing angle. The controller may compute the location of the tumor at each firing angle, and the computed location may be used to control the operation of the MV therapeutic radiation system. In some variations, the location of a tumor may be represented by the location of a centroid of the tumor at each firing angle. Alternatively or additionally, tumor location and/or movement may be represented by the tumor contour or by certain dense, highly visible structures. In the cases where tumor regions are not readily visible in kV X-ray images (e.g., due to obstruction by background anatomical structures, insufficient contrast, etc.) other surrogates for tumor motion may be used. For example, motion of the thoracic diaphragm (which is easily identified in an X-ray image due to its high X-ray contrast relative to surrounding anatomical structures) and/or motion of an implanted fiducial marker may be tracked instead or in addition to motion of the tumor(s). Tumor images may be enhanced by subtracting the background image data from the kV images. Optionally, the tumor images can be further enhanced by a limited angle digital tomosynthesis, where images from few previous angles can be shifted-and-added. At each firing angle, the kV X-ray beam may be collimated using the kV-DMLC template computed previously. The kV imaging system may optionally conduct a full scan (e.g., continuously acquire image data at all firing angles across the patient body region to be treated) just prior to, or at the start of, a treatment session (e.g., before the MV radiation source is activated). Alternatively or additionally, the kV system may acquire image data between MV radiation source pulses.

The location of a tumor as calculated based on imaging data from the kV imaging system may be used to update the MV-DMLC templates, if needed. For example, if the imaging data acquired during a treatment session indicates that the tumor geometry and/or location has shifted considerably (e.g., exceeding a pre-determined threshold) from its geometry and/or location as determined in pre-treatment imaging sessions, the controller may update the MV-DMLC templates to reflect these changes. For example, if imaging data acquired during the treatment session indicates that the tumor centroid has shifted from a first location to another, the controller may re-calculate or re-derive the MV-DMLC templates to reflect that centroid movement.

Figure 2B:
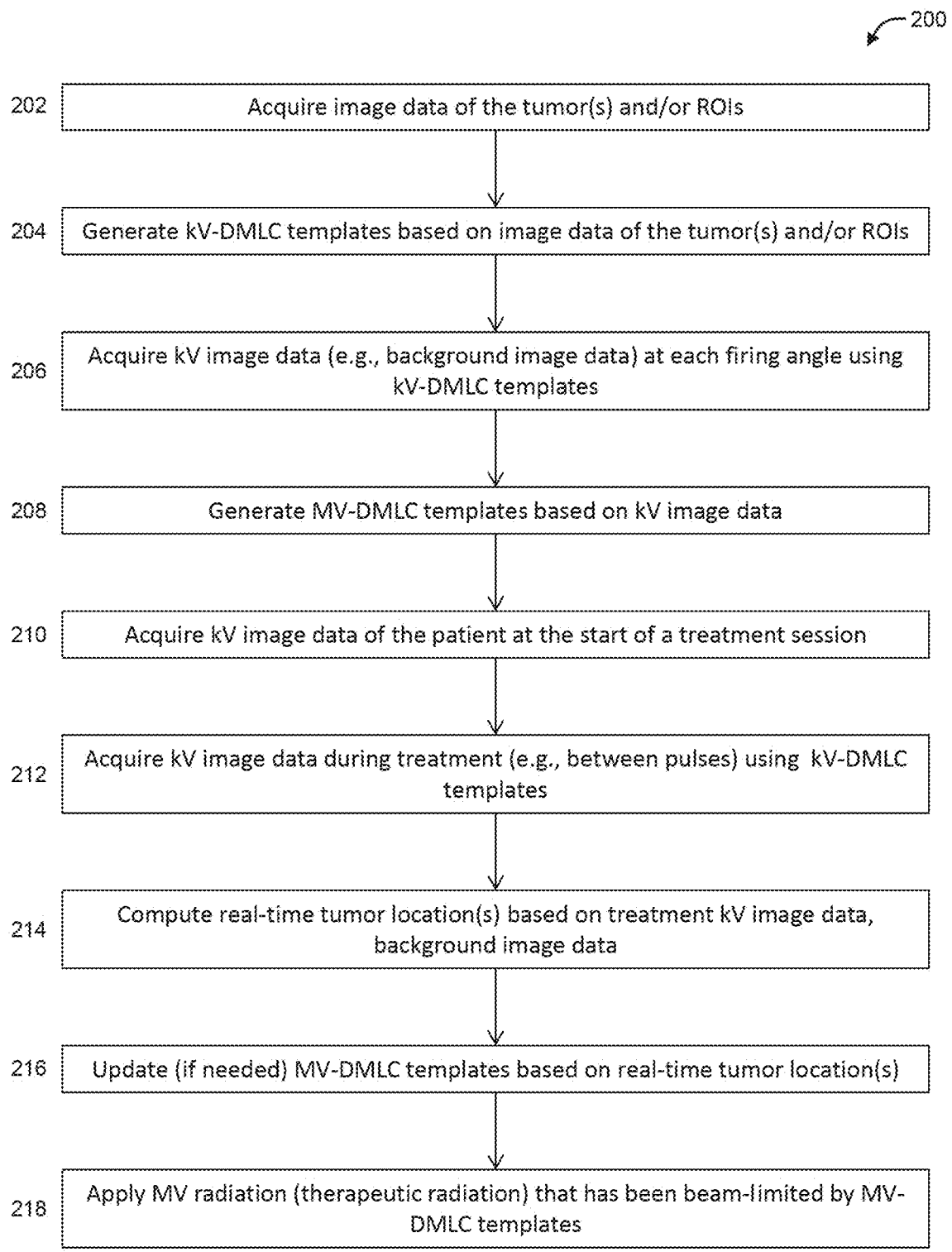
FIG. 2B is a flowchart depiction of one variation of a method for real-time tumor tracking and radiation therapy.

One variation of a method for real-time tumor tracking and treatment is depicted in FIG. 2B. The method 200 may comprise steps that are performed prior to a patient treatment session (e.g., pretreatment imaging sessions) and steps that are performed during a patient treatment session. The method 200 may comprise acquiring 202 image data of a patient tumor or ROI, generating 204 kV-DMLC templates based on image data from step 202, acquiring 206 kV image data of the patient tumor or ROI at each firing angle using the kV-DMLC templates from step 204, and generating 208 MV-DMLC templates based on the kV image data from any of the previous steps and/or any imaging data. Acquiring 202 image data of a patient tumor or ROI may be achieved using one or more imaging modalities, for example, CBCT imaging (or any type of CT imaging, tomographic or otherwise), MRI, ultrasound, X-ray images, etc. Acquiring 206 kV images may comprise moving an imaging system (e.g., such as a system depicted in FIGS. 1A-1B) to each firing angle or position around a patient area, adjusting the leaves of a kV DMLC in accordance with the generated kV-DMLC templates for each firing angle, applying a kV radiation beam (which has been beam-limited by the kV DMLC) to the patient, and using the kV detector to acquire image data for each firing angle. In some variations, steps 202-208 of method 200 may be performed before a treatment session (e.g., minutes, days, weeks, months before a treatment session). The method 200 may optionally comprise acquiring 210 image data of the patient at the start of a treatment session. The image data acquired may be a CBCT scan, tomographic scan, and/or limited-angle tomosynthesis scan. These image data may be used for registering the position of the patient with respect to the radiation therapy system, and/or updating any DMLC templates (either or both the kV DMLC and MV DMLC templates), and/or calibrating the radiation therapy system. The method 200 may further comprise acquiring 212 kV image data of the tumor or ROI during treatment using the previously-generated kV-DMLC templates, computing 214 real-time tumor geometry and/or location based on imaging data from step 212, updating 216 (if needed) the MV-DMLC templates based on real-time tumor geometry and/or location data from step 214, and applying 218 MV radiation beams (which have been beam-limited by the MV DMLC) to the patient. Acquiring 212 kV image data during treatment may take place between MV radiation beam pulses. Steps 212-218 may be repeated as the gantry rotates the kV imaging system and the MV therapeutic radiation system to all of the firing angles or positions around the patient area, until a desired time point and/or fluence has been delivered. The latency between acquiring 212 kV image data at a particular firing angle and applying MV radiation 218 at that firing angle may depend at least in part on the relative locations of the kV imaging system and the therapeutic radiation system, the gantry rotation speed, and the number of and angular distribution of firing angles or positions around the patient region. In some variations, the latency between steps 212 and 218 may be about 3 seconds or less, about 2 seconds or less, about 1 second or less, about 500 ms or less, or about 100 ms or less.

Method of Generating kV-DMLC Templates

Figure 3A:
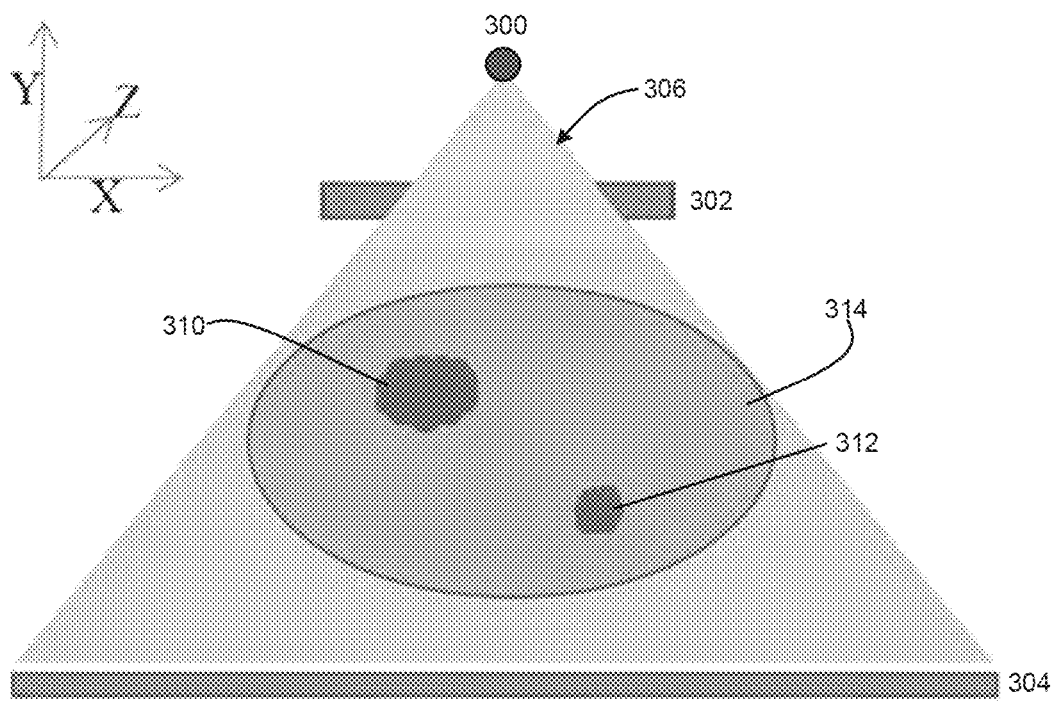
FIG. 3A is a schematic depiction of a CBCT scan with a full field-of-view (FOV).
Figure 3B:
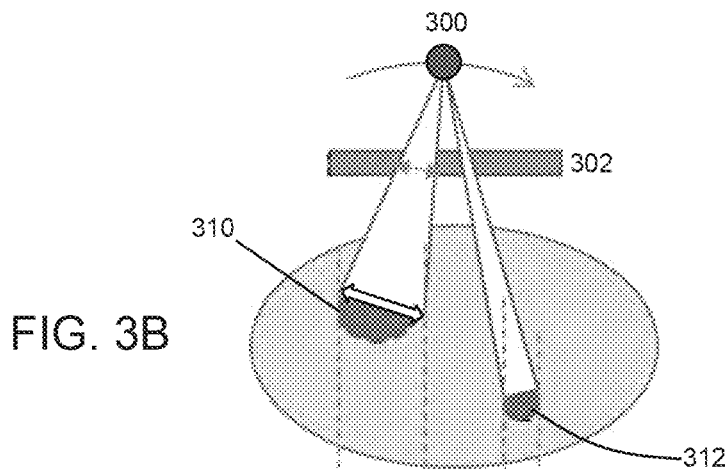
FIG. 3B is a schematic depiction of a back-projected kV DMLC, where the 2D projections of the tumor shapes from FIG. 3A are back-projected to the DMLC.
Figure 3C:
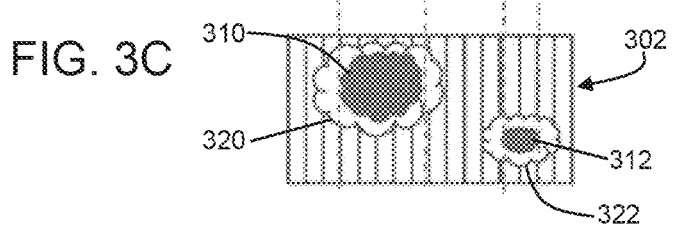
FIG. 3C is a schematic depiction of a variation of a set of kV DMLC templates with added margins for the motions and imaging (beam eye view).

FIGS. 3A-3C are schematic representations of one method of generating kV-DMLC templates using images acquired using cone beam CT (CBCT) and/or diagnostic 3D CT images (e.g., steps 202-204 of FIG. 2B). A controller may be configured to use image data from CBCT scans to determine tumor locations and tumor boundaries, and/or may be configured to calculate a tumor motion envelope. The tumor boundaries and/or tumor motion envelope data may be used to create set of kV-DMLC templates that correspond with the geometry (e.g., as may be determined by the measured tumor boundaries) and/or location. Each template in the set of kV-DMLC templates may correspond to the positions of the leaves of the kV DMLC at a particular firing angle. The set of kV-DMLC templates may comprise kV-DMLC templates of all firing angles around the patient area. These motion-enveloped tumor templates may be used to collimate the kV X-ray beam when acquiring imaging data of the patient. FIG. 3A depicts a 3D-CBCT scan using a kV X-ray system comprising a kV X-ray source 300, a kV DMLC 302, and a kV detector 304. The kV DMLC may be disposed within a beam path 306 of the kV X-ray source 300 and the kV detector 304 may be located across from the kV X-ray source 300. Many or all of the leaves of the kV DMLC 302 may be in the open configuration (e.g., wide-field or full-field irradiation). For example, the kV DMLC 302 may be fully open to cover the full patient field of view, including the tumor regions 310, 312 of patient 314. In this process, 3D volume image is reconstructed and corresponding set of 2D projections at the defined gantry angles are created by digitally reconstructed radiographs. In some variations, the imaging slice width in the Z-direction may be selected to closely approximate the size of the tumor (e.g., just large enough to cover the tumors plus a margin in the axial direction), as depicted in FIG. 3C, which may help to reduce X-ray scatter. For example, for tumors contained in 8 cm slice width, the kV DMLC may be configured to provide a FOV of 10 cm (Z)×40 cm (X) at ISO. The shape of the tumors may be extracted from the 3D-CBCT, the tumor cross-section area perpendicular to the central X-ray can be determined (e.g., projection of the tumor along the axis of the kV X-ray). As illustrated in FIGS. 3B and 3C, the kV-DMLC template may have an opening shape that is the same (or similar) shape as the scaled cross-section area of the tumor. FIG. 3C shows an example of a kV-DMLC template where the leaves of the kV DMLC 302 are positioned such that the opening(s) 320, 322 may be shaped like the two tumors, 310 and 312, from beam's eye view. As shown in FIG. 3C, a margin, e.g., about 1 cm, can be added to the tumor cross-section area for the kV X-ray imaging. The scaling factor may be the ratio of the source to DMLC to the source to the plane of the tumor cross-section. A plurality of kV-DMLC templates may be created for each tumor at each firing angle. For example, the controller may create a set of kV-DMLC templates comprising a kV-DMLC template for every firing angle of a radiation therapy system, where the leaf configuration of each kV-DMLC template is such that the shape of the opening approximates the cross-sectional view of the tumor(s) (e.g., projection of the tumor(s)) at that firing angle.

Method of Generating MV-DMLC Templates and Background Imaging

FIGS. 4A-4G are schematic representations of one variation of a method of acquiring image data using the kV-DMLC templates (e.g., steps 206-208 of FIG. 2B). The method depicted in FIGS. 4A-4G may be used to, for example, acquire background images at each firing angle using the kV-DMLC templates, which may contain information relating to the geometry and location of non-moving and bony structures. Such background images may be used for background subtraction, for example, to enhance images acquired during a treatment session. Image data acquired using the method depicted in FIGS. 4A-4G may not be motion blurred (as compared to the image represented in FIG. 3A), and may be used by the controller to generate a set of MV-DMLC templates that may be used in a treatment session. Alternatively or additionally, a set of MV-DMLC templates comprising a MV-DMLC template for every firing angle may also be derived from diagnostic 4D CT images. For example, MV-DMLC templates may be generated by back projecting the tumor shape(s) at every firing angle, and matching the MV-DMLC leaf configuration with the shape of the tumor backprojection at each firing angle (i.e., the shape of the opening of a MV-DMLC template for a particular firing angle corresponds with the geometry of the tumor backprojection at that firing angle).

Figure 4A:
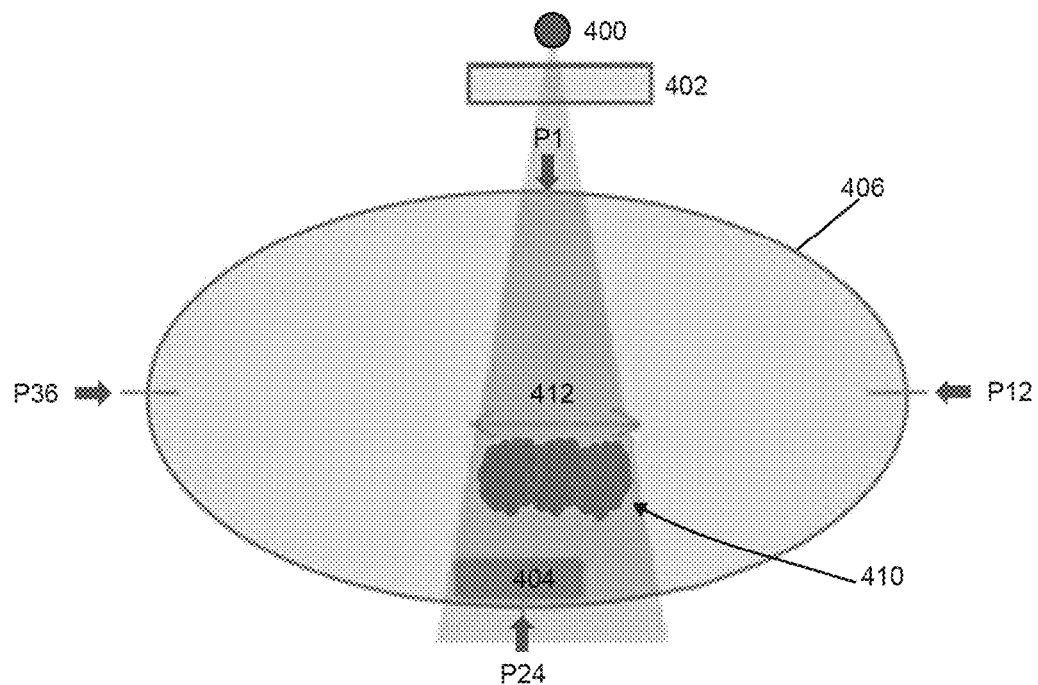
FIGS. 4A-4G is a graphic depiction of one variation of a method for creating background images for image enhancement and for generating MV-DMLC templates.

FIG. 4A depicts the use of the kV-DMLC templates to collimate the X-ray imaging beam to the tumor (or multiple tumors). A kV imaging system may comprise a kV X-ray source 400, a kV DMLC 402, and a kV detector (not shown). The kV DMLC may be disposed within a beam path of the kV X-ray source 400 and the kV detector (not shown) may be located across from the kV X-ray source. The kV imaging system components may be mounted on a rotatable gantry 406. In this example, the system may comprise 48 firing positions or angle (position 1, position 12, position 24, and position 36 are depicted in FIG. 4A as P1, P12, P24, and P36). At each firing angle, the tumor 410 may be imaged multiple times, which may capture many (if not all) phases of the tumor motions (e.g., tumor 410 moving to different positions along arrow 412, relative to a stationary bone structure 404) through multiple gantry rotations. Collimating the X-ray imaging beam using the kV-DMLC templates may help to reduce X-ray dose while still acquiring a dense set of tumor images.

Figure 4B:
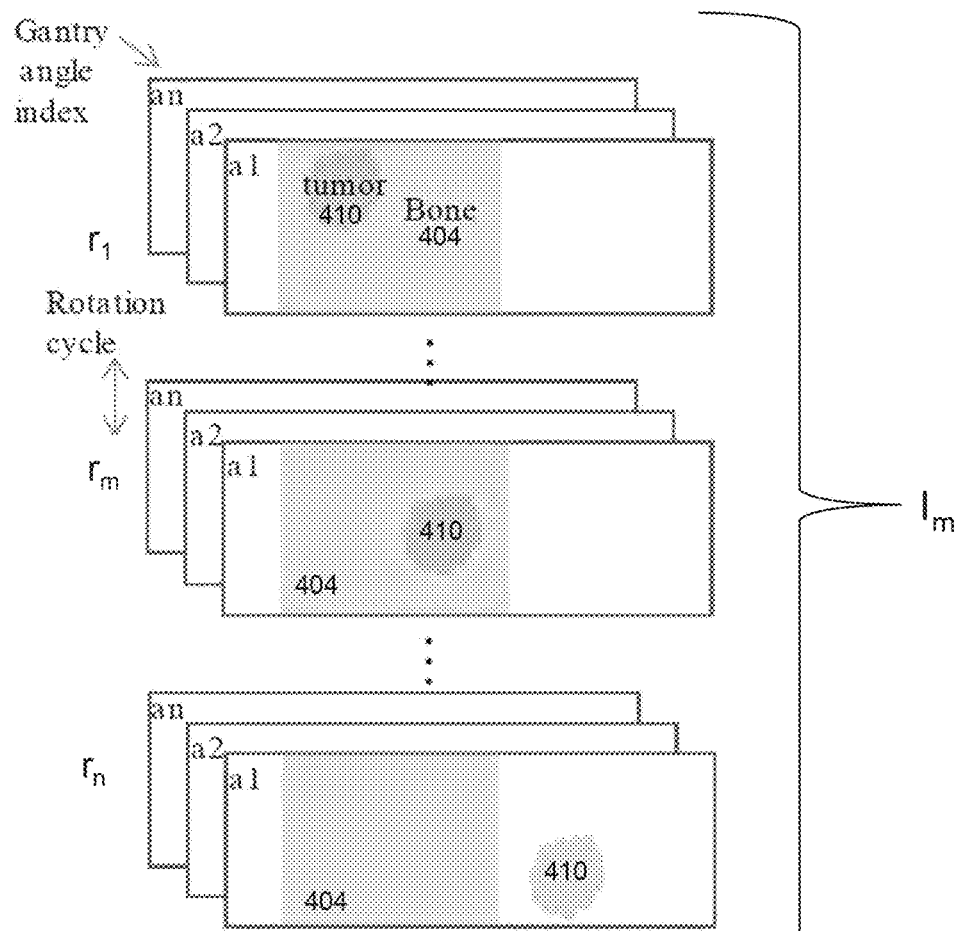

FIG. 4B depicts images ($I_m$), from multiple firing angles and over multiple gantry rotations acquired by the kV imaging system. Images $I_m$ may be 2D projections of the tumor 410 (and any adjacent bone structure) at each of the firing angles over multiple gantry rotations. In order to capture all positions of a moving tumor (e.g., during a breathing cycle), a sufficient number of images should be acquired at each firing angle. In some variations, images may be acquired at an imaging rate of 1.25 frame/second at each firing angle, and since this rate is higher the typical breathing rate of 0.25 cycle per second, all the motion phases may be captured within multiple gantry rotations. Images $I_m$ may comprise one or more sets of images $r_m$ (where m=1 to number of desired gantry cycles, e.g., number of cycles to capture all motion phases of a breathing cycle from most firing angles). Each set of images $r_m$ may comprise one or more sets of image data acquired at each firing angle $a_n$ (n=1 to n=number of firing angles or positions, e.g., 48 firing angles).

Figure 4C:
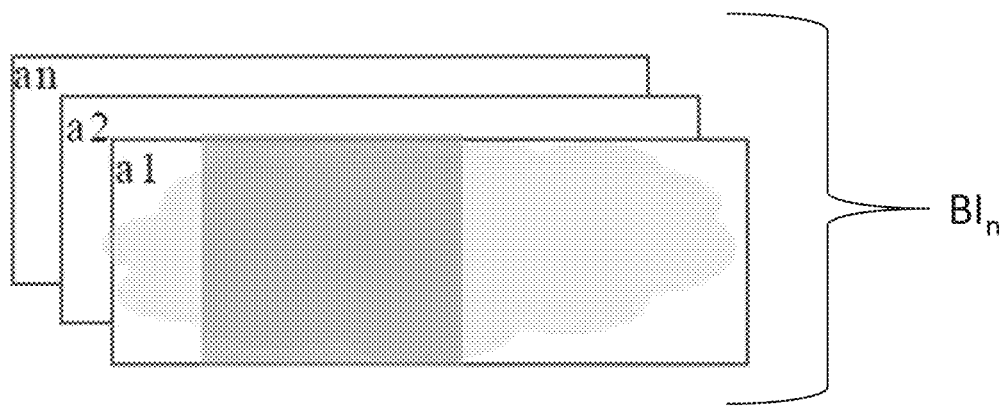

FIG. 4C depicts a set of background images $BI_n$ (n=1 to n=numbering of firing angles). Each background image BI may be derived by averaging all of the images from the same firing angle n across all gantry rotations m. For example, for an image data set acquired over m=10 gantry rotations ($I_{10}$), $BI_1$ may be the average of image data acquired at firing angle n=1 ($a_1$) for gantry rotations m=1-10. Tumor motion (e.g., a tumor envelope that may be schematically represented by the cloud-like shape in FIGS. 4C-4F) may be blurred out as the images are averaged, while the contrast of non-moving anatomical structures (e.g., bone structures) may be enhanced. For example, for the imaging and treatment of lung tumors, a nearly uniform background image of motion envelope may be achieved due to the averaging of large number of images from all phases of the lung motion.

Figure 4D:
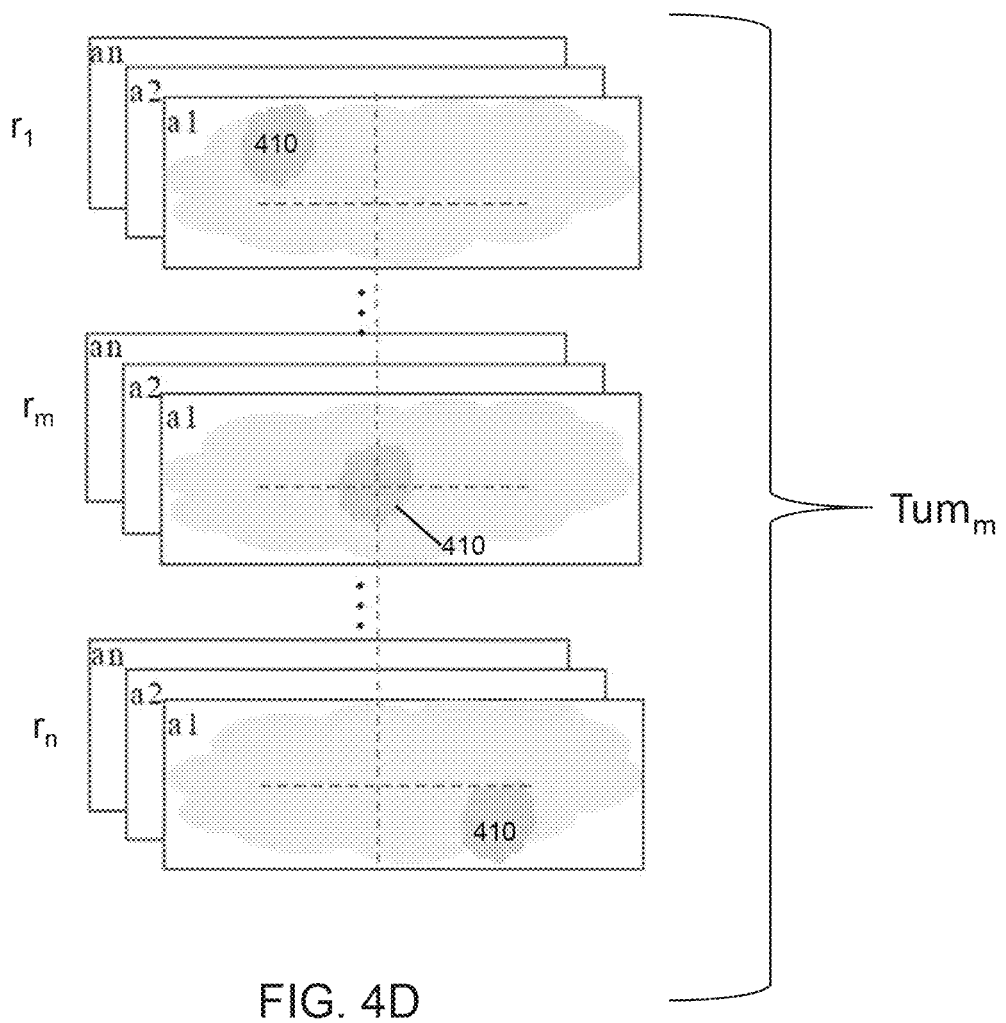
Figure 4E:
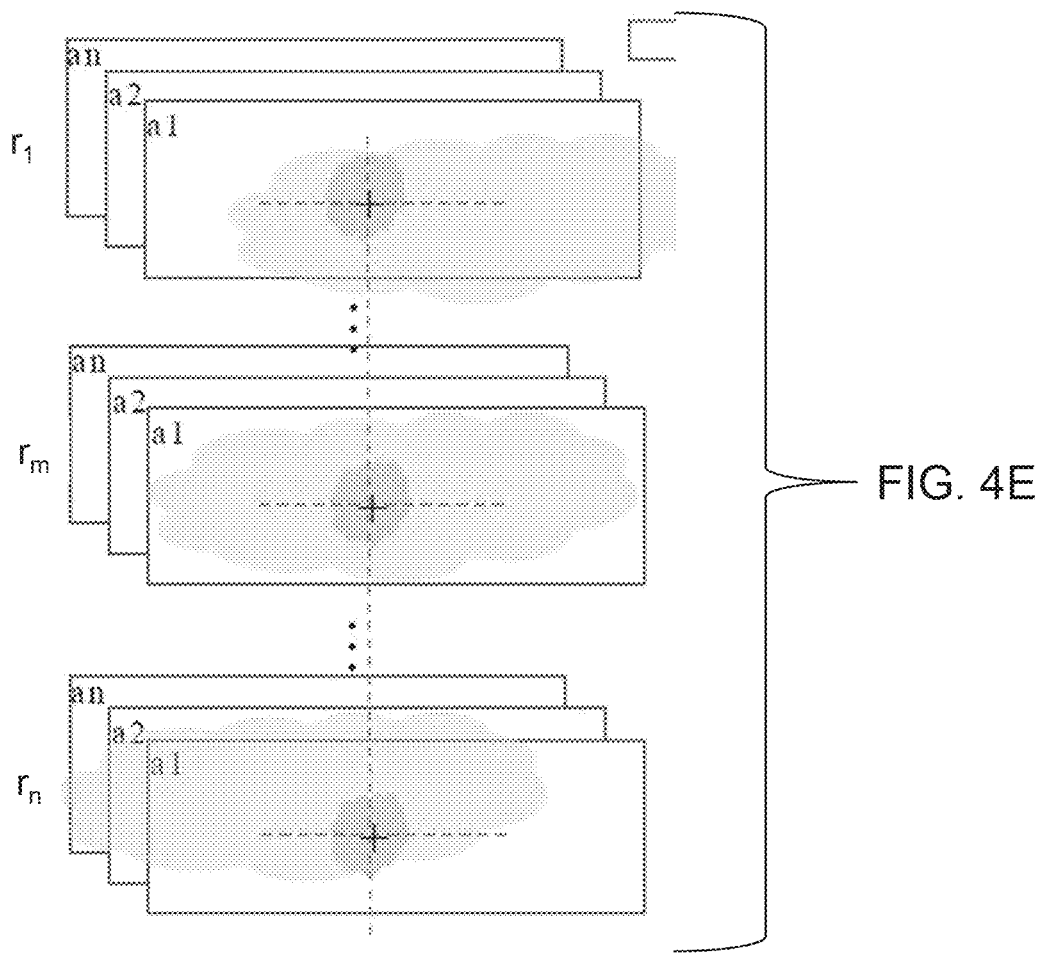
Figure 4F:
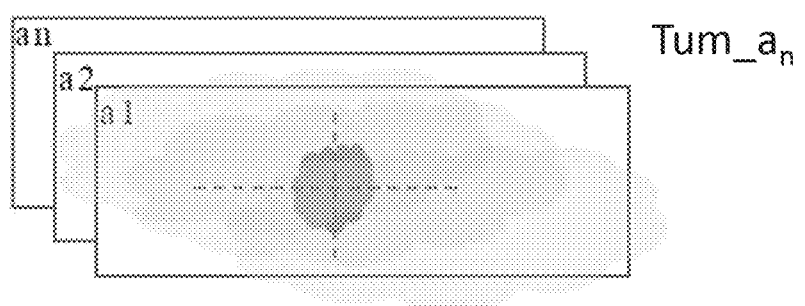

FIG. 4D depicts tumor images $Tum_m$, which may be derived from subtracting background images $BI_n$ from images $I_m$ ($Tum_m=I_{m,n}-BI_n$). Tumor images $Tum_m$ may comprise a set of images (e.g., 2D projections) of the tumor at multiple firing angles and over multiple gantry rotations. Background clutter in the image (e.g., non-moving anatomical structures and/or boney regions) may be largely removed. Subtracting out the background from the kV image data may help to improve tumor contrast.

After the tumor images $Tum_m$ have been enhanced using background subtraction, the centroid of the tumor (annotated by +) may be computed. The tumor contour may optionally be further delineated. The controller may shift and align the tumor centroid to the mean tumor centroid in rotation $r_m$. Cumulatively, by aligning the tumor centroid of multiple images, the tumor centroid may be shifted toward the center of the image. After aligning the tumor images, they may be averaged together to enhance tumor visibility. The images in FIG. 4E may be averaged together to obtain the images in FIG. 4F. That is, the image data acquired at gantry angle n across multiple gantry rotations m may be averaged together to obtain an average tumor image $Tum\_a_n$. The motion envelope (e.g., tumor envelope) may be further blurred in average tumor image $Tum\_a_n$.

Figure 4G:
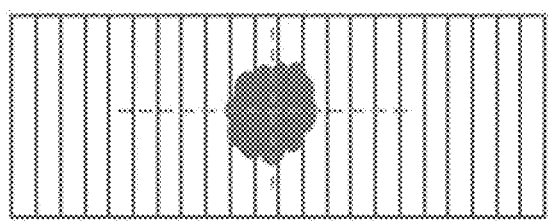

In some variations, MV-DMLC templates such as the one depicted in FIG. 4G may be derived based on $Tum\_a_n$. The tumor boundary may be defined from $Tum\_a_n$. MV-DMLC templates may be created without the tumor motion envelope. The controller may generate a set of MV-DMLC templates comprising an MV-DMLC template for each firing angle, the MV-DMLC template corresponding to the 2D projection of a tumor at that firing angle.

Method of Tumor-Tracking During Radiation Therapy

One variation of a method of real-time tumor tracking, image data processing and MV firing (e.g., steps 212-218 of FIG. 2B) is schematically represented in FIGS. 5A-5G. In this variation, the controller computes the centroid of a tumor, and tracks the changes in centroid location. Changes in the location of the tumor centroid may be used to change or MV-DMLC templates during the treatment session. For example, a shift of the tumor centroid detected in the kV image data may be used to update MV-DMLC templates to have a corresponding shift. In some variations, the shape and location of the opening in the MV-DMLC (e.g., the shape and location of the radiation-transmitting portion of the DMLC) may be calculated before a treatment session, and may be, in some variations, the MV-DMLC templates derived using the method depicted in FIGS. 4A-4G. The therapeutic radiation source (e.g., MV X-ray source) may fire treatment X-ray pulses while the MV DMLC is changing leaf configuration (e.g., changing between pre-determined MV-DMLC templates and/or changing between a pre-determined MV-DMLC template and an MV-DMLC template that has been updated to reflect changes in the tumor centroid), and/or may fire treatment X-ray pulses after the MV DMLC has reached the leaf configuration that corresponds to a pre-determined or updated MV-DMLC template. The radiation therapy system may repeat the steps depicted in FIGS. 5A-5G for all the firing angles of the gantry, over one or more gantry rotations. The gantry may rotate multiple times until the prescribed dose to the tumors has been attained and/or a prescribed fluence has been delivered.

Figures 5A, 5B:
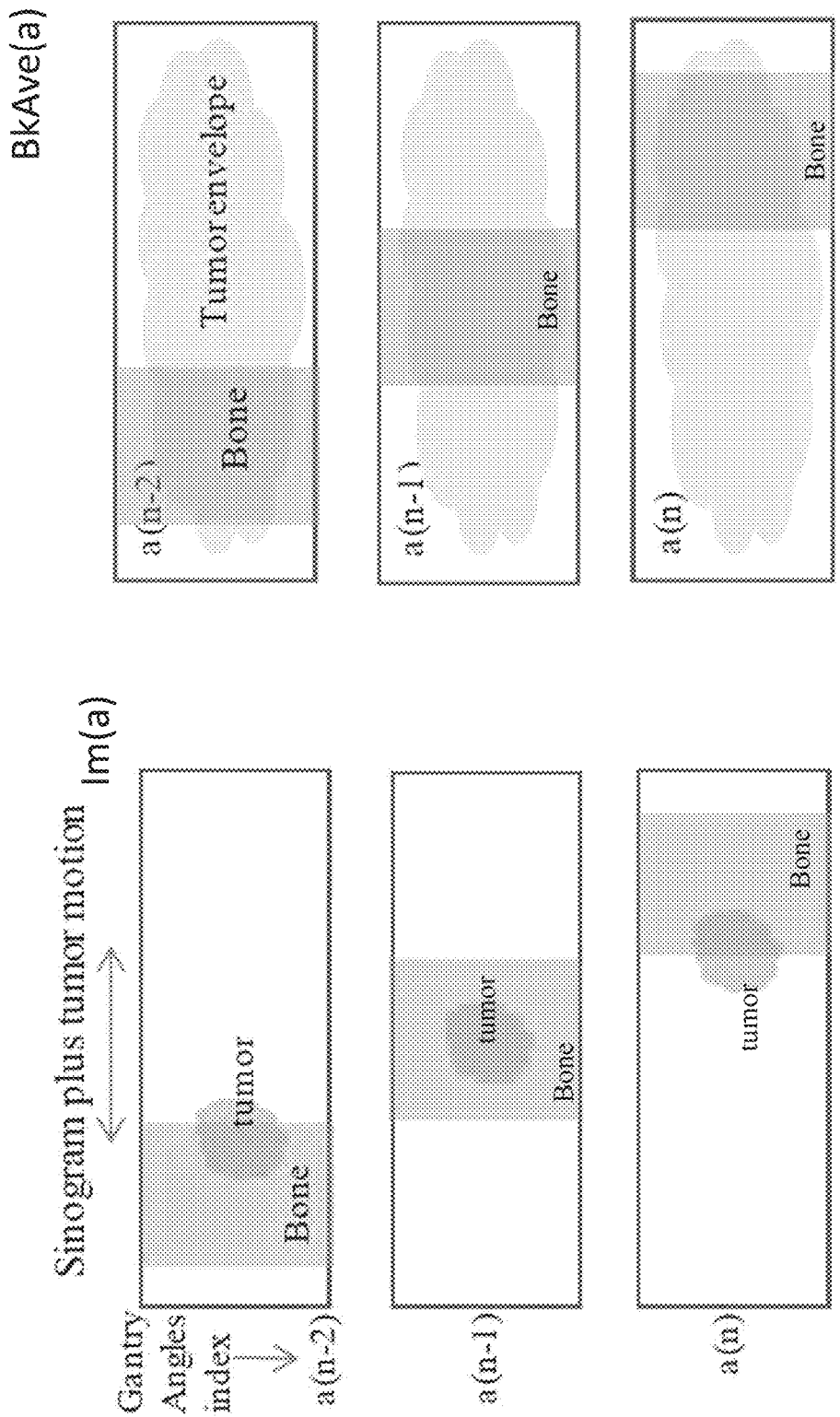
FIGS. 5A-5G is a graphic depiction of one variation of a method for real-time tumor location and radiation therapy.

One variation of a method for real-time tumor tracking and treatment using, for example, a radiation therapy system of FIG. 1A may comprise acquiring kV image data during a treatment session. FIG. 2A represents one variation of the timing of kV image acquisition relative to MV radiation treatment. FIG. 5A depicts a representative set of images Im(a) comprising image data collected at each firing angle or position a(n). The images Im(a) may be obtained by applying a kV X-ray beam that has been collimated with the kV DMLC templates to the patient. The image Im at a(n) represents image data collected by the kV imaging system at the current location (i.e., firing angle n) of the kV imaging system. The image Im at (n–1) and image Im at (n–2) represent image data collected by the kV imaging system when it was located at previous firing angles. The shaded region of the images Im represent a bone structure. The apparent shift of the bone structure across the images may be due to the sinogram (i.e., the position of the bone appears to vary because the image data is acquired from different firing angles using kV-MLC templates that are tailored to each firing angle). The apparent shift of the tumor across the images may be due to the sinogram and as well as actual motion of the tumor (e.g., due to breathing motions).

Figure 5C:
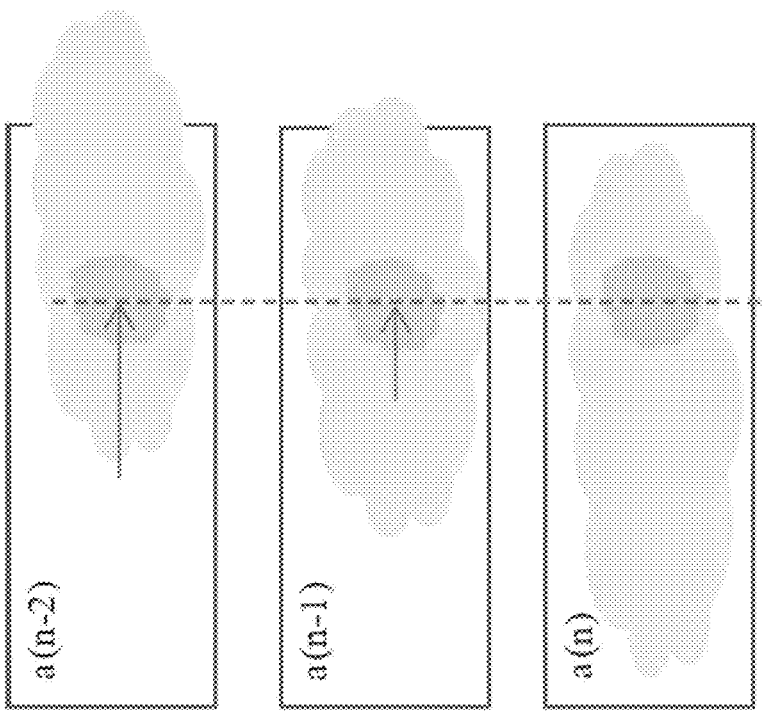

To help increase the contrast of the tumor edges and/or to otherwise enhance the image and/or improve the precision of tumor centroid calculations, background features in the images Im(a) may be subtracted out. FIG. 5B depicts representations of background images BkAve(a) that may be used to remove background features from the images Im. In some variations, BkAve(a) may be the background images $BI_n$ as described and depicted in FIG. 4C. Optionally, the background images BkAve(a) may be modified by the controller to shift of bony structure to match any shifts in bony structures in the images Im. Re-alignment of the bony structures in background images BkAve(a) to the current bone position in images Im may be performed before the subtraction. FIG. 5C depicts the set of images ImSub(a) derived from subtracting background images BkAve(a) from images Im(a) (e.g., ImSub(n) may represent an image before tomosynthesis enhancement). The contour of the tumor, as well as the centroid of the tumor (+), may be computed from ImSub(a).

Figure 5D:
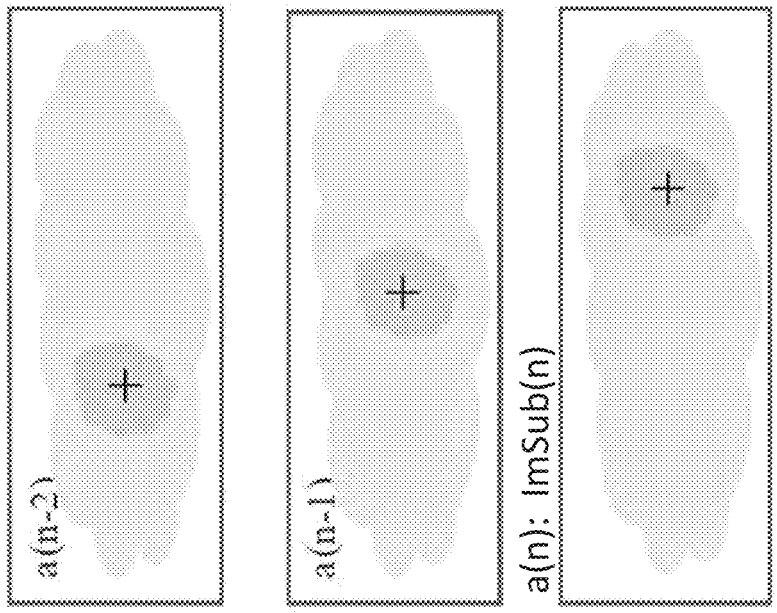

The tumor centroid of the images may be shifted such that the tumor centroid of the Im at a(n–2) and Im at a(n–1) is aligned to that of Im at a(n). In some variations, the tumor centroid of Im at a(n) may reflect sinogram motion (examples of which are provided in FIGS. 6A and 6B, to be described further below). The shifted images Imshift(a) of images Imsub(a) are depicted in FIG. 5D. There may be, in some situations, possible tumor motion (e.g., a tumor envelope that may be schematically represented by the cloud-like shape in FIGS. 5B-5D) from between images Imshift at a(n–2) and Imshift at a(n–1) to Imshift at a(n). For example, under the conditions described in FIG. 1B, the tumor motion between Imshift at a(n–2) to Imshift at a(n) may be about 0.2 mm and the tumor motion between Im shift at a(n–1) to Imshift at a(n) may be about 0.1 mm Images Imshift may reflect this tumor motion, or may not reflect this tumor motion.

Figures 5E, 5F, 5G:
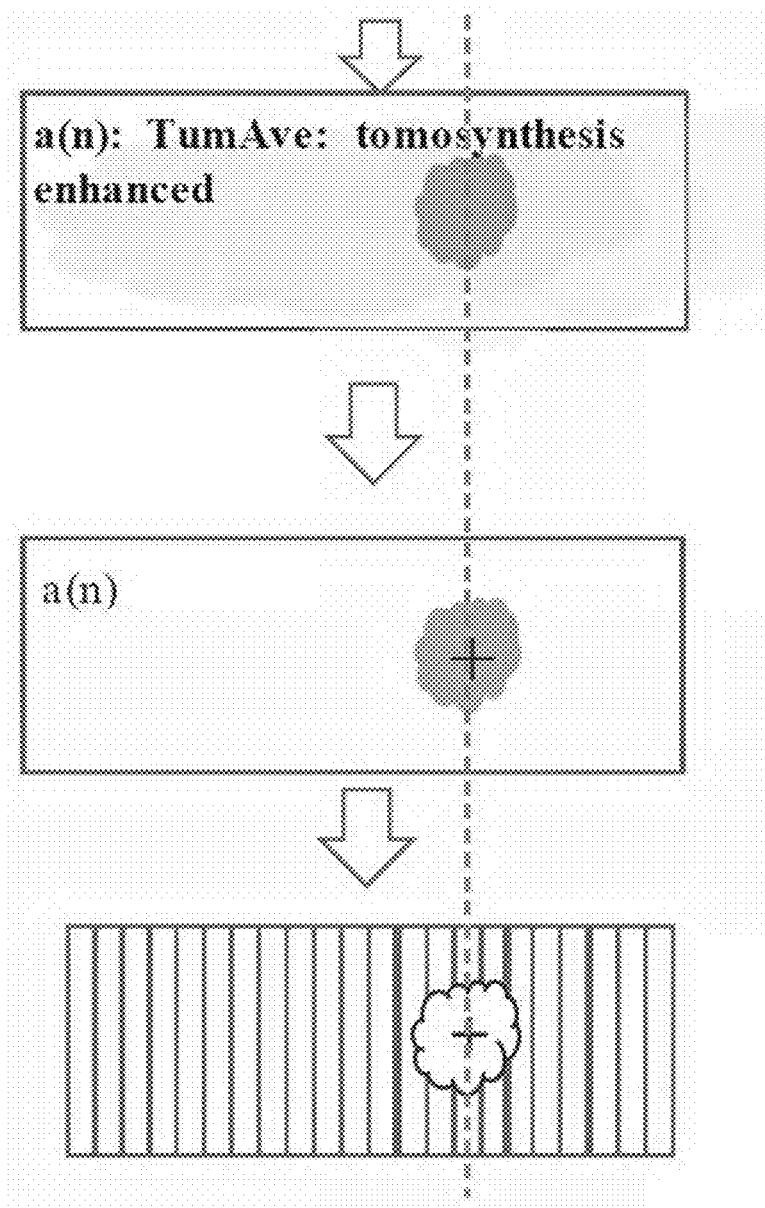

The image of the tumor may be further enhanced by averaging the shifted images Imshift depicted in FIG. 5D. The result of averaging the images TumAve(n), for example by shifting and adding, may be average tumor image TumAve(n), as depicted in FIG. 5E. Similar tumor images may be obtained using limited angle tomosynthesis methods and computations. However, as compared to conventional tomosynthesis, tumor image TumAve(n) may have better defined tumor edge contrast, since background anatomical structures have been subtracted out. The tumor contour and centroid at gantry firing angle a(n) may be calculated based on tumor image TumAve(n), as depicted in FIG. 5F. The MV-DMLC template for the firing angle a(n) may be updated (e.g., from the pre-calculated configuration depicted in FIG. 5G) according to the updated tumor contour and centroid of FIG. 5F. The MV radiation source may then fire radiation pulses that have been beam-limited by the MV DMLC toward the patient.

EXAMPLES

Figure 6A:
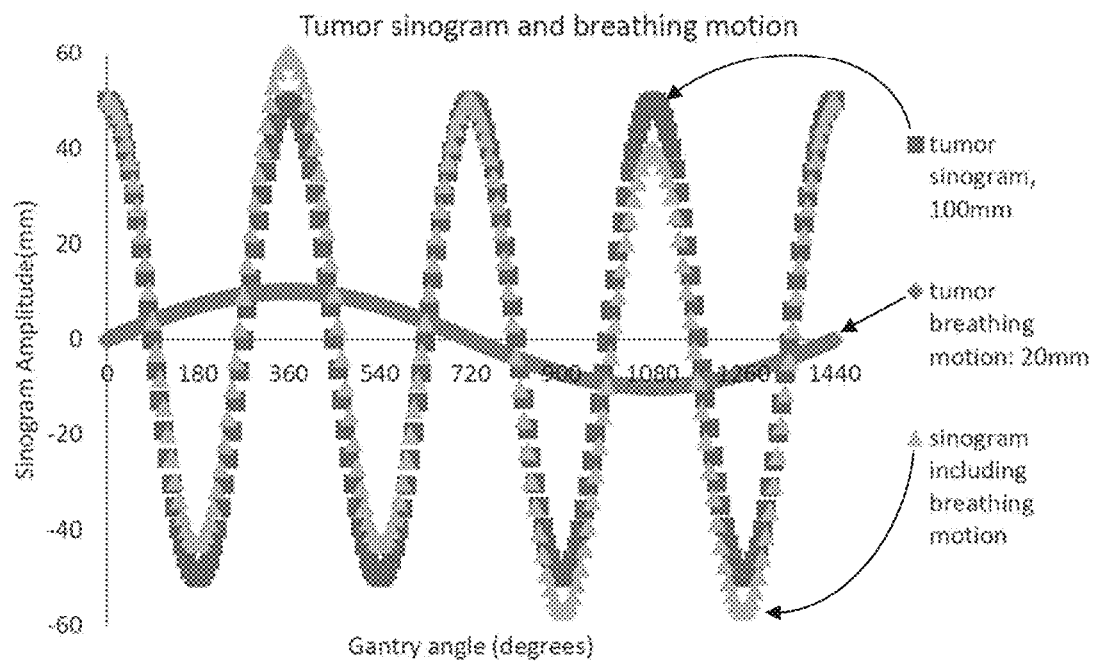
FIG. 6A depicts one example of a plot of sinogram amplitude as a function of gantry angle.
Figure 6B:
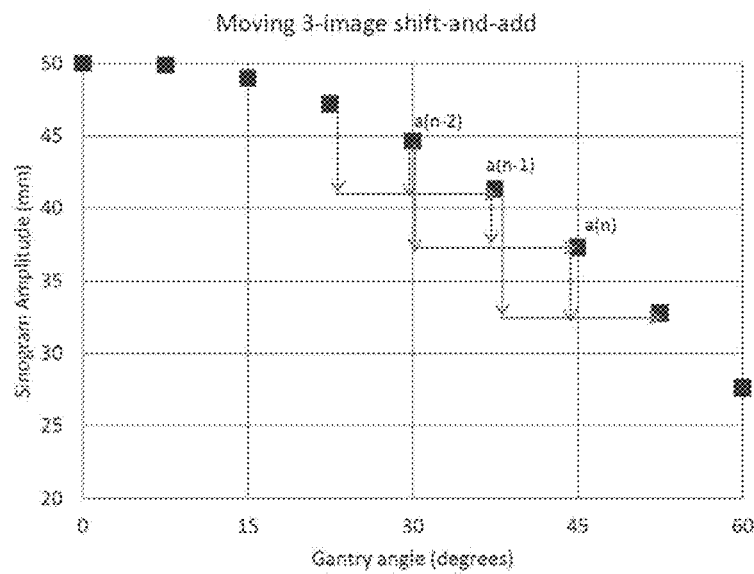
FIG. 6B depicts one example of a moving shift-and-add plot of sinogram amplitude as a function of gantry angle.

FIGS. 6A and 6B are example plots of sinogram amplitude as a function of gantry angle. The sinogram amplitude in these plots may represent the displacement of a tumor centroid over a breathing cycle. These examples reflect the treatment time to deliver 10 Gy dose to a tumor, using a 6 MV linac with an output of about 10 Gy/minute at 1.5 cm water depth or Dmax at 300 Hz pulse rate, which is 0.55 mGy per X-ray pulse. In this example, the linac can fire two pulses at one firing angle. For these plots, it is also assumed that the tumor is located at 10 cm from the skin on all direction and the beam attenuation is 55% from the Dmax at the tumor depth. The dose rate is 0.55 mGy/pulse×55%=0.3 mGy/pulse at the tumor depth, or 0.6 mGy per firing angle. This would yield a dose per gantry rotation of about 0.6 mGy×48=28.8 mGy. The number of gantry rotations needed to deliver 10 Gy dose to the tumor may be 10 Gy divided by 0.0288 Gy/rotation, or 347 rotation. With one rotation per 0.8 second, the treatment time would be 277 second, or 4.6 minutes.

FIG. 6A depicts a simplified sinogram for the centroid of a tumor 50 mm from the ISO center with breathing amplitude of 20 mm. The sinogram is a graphical representation of tumor projection location as function of the projection angles. The sinogram of a static tumor may be a simple sinusoidal curve. In contrast, the sinogram for a moving tumor the sinogram may deviate from a sinusoidal curve. The curve delineated with squares represents the sinogram without the breathing motion, the curve delineated with diamonds represents the sinogram with tumor breathing motion of about 20 mm amplitude, and the curve delineared with triangles represented the sinogram with the breathing motion.

FIG. 6B represents a moving 3-image shift-and-add scheme for circular tomosynthesis. The images a(n−2) and a(n−1) are shifted down to align with the image a(n), as described in FIG. 5D.

The invention claimed is:

1. A radiation therapy system comprising:
a rotatable gantry;
an imaging system mounted on the gantry, wherein the imaging system comprises an imaging radiation source mounted at a first location on the gantry and a first multi-leaf collimator located in a radiation beam path of the imaging radiation source;
a therapeutic radiation system mounted on the gantry, wherein the therapeutic radiation system comprises a therapeutic radiation source mounted at a second location on the gantry and a second multi-leaf collimator located in a radiation beam path of the therapeutic radiation source; and
a controller configured to send instructions to the imaging system and the therapeutic radiation system to:
acquire image data of a region-of interest (ROI) using the imaging system to compute a real-time location of the ROI during a treatment session; and
apply radiation to the real-time location of the ROI during the same treatment session using the therapeutic radiation source.

2. The system of claim 1, wherein the applied radiation has been updated according to the acquired image data of the ROI.

3. The system of claim 1, wherein image data is acquired by setting the leaf positions of the first multi-leaf collimator, and wherein radiation is applied by setting the leaf positions of the second multi-leaf collimator according to the real-time location of the ROI.

4. The system of claim 3, wherein acquiring imaging data further comprises the use of an MLC template, and wherein the controller is further configured to compute an imaging system MLC template for each firing position of the imaging radiation source.

5. The system of claim 4, wherein the imaging system MLC template at each firing position of the imaging radiation source has a shape that corresponds with a projection of the ROI at that firing position.

6. The system of claim 5, wherein the imaging system MLC template is generated from CT image data.

7. The system of claim 5, wherein the shape includes movement margin around the projection of the ROI.

8. The system of claim 4, wherein the controller is further configured to calculate a therapeutic radiation system MLC template for each firing position of the therapeutic radiation source, and wherein the therapeutic radiation system MLC template has a shape that corresponds with a projection of the ROI at that firing position.

9. The system of claim 8, wherein the shape of therapeutic radiation system MLC template is updated using the real-time location of the ROI.

10. The system of claim 9, wherein updating the therapeutic radiation system MLC template comprises shifting the shape to the real-time location of the ROI.

11. The method of claim 3, wherein the ROI is a lung tumor.

12. The system of claim 1, wherein the controller is configured to rotate the gantry such that the imaging system sweeps a portion of the ROI before the therapeutic radiation system applies radiation to the portion of the ROI.

13. The system of claim 1, wherein the imaging system has a field of view and the therapeutic radiation system has a therapeutic plane that is coplanar with the imaging system field of view.

14. A method for real-time tracking of a patient tumor during radiation therapy, the method comprising:
acquiring image data of a region-of interest (ROI) using radiation emitted by an imaging radiation source through an imaging system multi-leaf collimator aperture, wherein the aperture has a shape defined by an imaging system MLC template;
computing a real-time location of the ROI based on the acquired image data; and
applying therapeutic radiation to the real-time location of the ROI.

15. The method of claim 14, wherein the therapeutic radiation is generated by a therapeutic radiation source and shaped by a therapeutic radiation system multi-leaf collimator aperture, wherein the aperture has a shape defined by a therapeutic radiation system MLC template that has been updated according to the real-time location of the ROI.

16. The method of claim 14, wherein the imaging system MLC template at each firing position of the imaging radiation source has a shape that corresponds with a projection of the ROI at that firing position.

17. The method of claim 16, wherein the imaging system MLC templates are generated from CT image data of the ROI.

18. The method of claim 16, wherein applying therapeutic radiation comprises adjusting an aperture of a therapeutic radiation source multi-leaf collimator, wherein the aperture has a shaped defined by a therapeutic radiation system MLC template that is derived from the imaging system MLC template, and emitting radiation through the aperture of the therapeutic radiation source multi-leaf collimator using a therapeutic radiation source.

19. The method of claim 18, further comprising updating the MLC template of the therapeutic radiation system according to the real-time location of the ROI.

20. The method of claim 19, wherein updating the MLC template of the therapeutic radiation system comprises shifting the aperture to the real-time location of the ROI.

\* \* \* \* \*